(12) United States Patent
Treichler et al.

(10) Patent No.: US 7,585,852 B2
(45) Date of Patent: Sep. 8, 2009

(54) COBALAMINE DERIVATIVES USEFUL FOR DIAGNOSIS AND TREATMENT OF ABNORMAL CELLULAR PROLIFERATION

(75) Inventors: Hans-Jörg Treichler, Känerkinden (CH); Roger Alberto, Winterthur (CH); Robert Waibel, Ricketwil (CH); Martin T. Küenzi, Muttenz (CH); Jakob Nüesch, Arlesheim (CH); Stefan Mundwiler, Aarau (CH); Dave R. van Staveren, Rotterdam (NL)

(73) Assignees: Solidago AG, Bern (CH); Zurich, Universtitat, Zurich (CH); Paul Scherrer Institut, Villigen Psi (CH)

( * ) Notice: Subject to any disclaimer, the term of this patent is extended or adjusted under 35 U.S.C. 154(b) by 26 days.

(21) Appl. No.: 10/583,760

(22) PCT Filed: Dec. 21, 2004

(86) PCT No.: PCT/EP2004/053628

§ 371 (c)(1),
(2), (4) Date: Jun. 21, 2006

(87) PCT Pub. No.: WO2005/061527

PCT Pub. Date: Jul. 7, 2005

(65) Prior Publication Data

US 2007/0155692 A1     Jul. 5, 2007

(30) Foreign Application Priority Data

Dec. 22, 2003   (EP) .................................. 03405913

(51) Int. Cl.
*A61K 31/714*   (2006.01)
*C07H 23/00*   (2006.01)
(52) U.S. Cl. ....................................... 514/52; 536/26.4
(58) Field of Classification Search ................ 514/52; 536/26.4

See application file for complete search history.

(56) References Cited

U.S. PATENT DOCUMENTS 5,739,313 A * 4/1998 Collins et al. ............. 536/26.44
6,797,521 B2 * 9/2004 Grissom et al. ............. 436/505
2003/0144198 A1 7/2003 Collins et al.

FOREIGN PATENT DOCUMENTS

WO        95/27723       10/1995
WO   WO 95/27723    * 10/1995

OTHER PUBLICATIONS

The Merck Index, 1992, paes 86-107.*
Trisha Gura, Science, 1997, 278(5340), 1041-42.*

* cited by examiner

*Primary Examiner*—Shaojia Anna Jiang
*Assistant Examiner*—Ganapathy Krishnan
(74) *Attorney, Agent, or Firm*—Wenderoth, Lind & Ponack, L.L.P.

(57) ABSTRACT

The invention relates to cobalamin derivatives having no or low binding affinity to the transport protein transcobalamin II (TCII) and retaining activity as a vitamin B12 substitute, optionally carrying a therapeutic and/or diagnostic agent, such as a radioactive metal. These compounds have a much reduced accumulation rate in blood and benign organs, such as kidney and liver, compared to the accumulation rate in neoplastic tissues, and are more rapidly eliminated from blood. The invention further relates to a method of diagnosis and a method of treatment of a neoplastic disease or an infection by microorganisms in a mammal by exposing the mammal to a period of a vitamin B12 free diet, and subsequently applying a cobalamin derivative of the invention carrying a diagnostic and/or therapeutic agent. By selecting cobalamin derivatives acting as vitamin B12 substitutes, the risk of the formation of resistant off-spring in neoplastic tissue is much reduced.

17 Claims, 6 Drawing Sheets

COBALAMINE DERIVATIVES USEFUL FOR DIAGNOSIS AND TREATMENT OF ABNORMAL CELLULAR PROLIFERATION

This application is a U.S. national stage of International Application No. PCT/EP2004/053628 filed Dec. 21, 2004.

FIELD OF THE INVENTION

The invention relates to methods for imaging and destroying rapidly proliferating undesirable cells in multicellular organisms.

BACKGROUND OF THE INVENTION

Abnormal cellular proliferation, notably hyperproliferation, is the source of numerous diseases, the most severe one being cancer. In the United States alone approximately 1.5 million people are diagnosed with cancer and 0.5 million die from it each year. The fight against cancer has seen some success but also numerous set-backs. Severe side-effects of anti-cancer drugs and the development of resistant off-spring of cancerous cells are major problems, as is the early and precise localization of tumours and metastasis.

Hyperproliferative cells, such as many cancerous cells, depend on an increased supply of nutrients, growth factors, energy and vitamins. Using the supply route of a vitamin, which is essential for cellular growth and is often in short supply, one might possibly transport drugs to these unwanted cells.

Cobalamin (Cbl), also known as Vitamin B12 and present as cyano-cobalamin (CN-Cbl), hydroxy-cobalamin (HO-Cbl) or aquo-cobalamin ($H_2O$-Cbl), is essential for life and its concentration in the body is very low. Higher organisms including humans have to get the vitamin from their food. The biosynthesis of cobalamin is limited to some prokaryotic organisms, such as anaerobic bacteria. Cobalamin is important for the proper function of the nervous system and is necessary for the proper metabolism of carbohydrates, proteins and fat. Cobalamin is utilized in essential intracellular metabolic pathways. As methyl-cobalamin (Me-Cbl), it functions as a cofactor for methionine synthase. As 5'-deoxyadenosyl-cobalamin (Ado-Cbl), it functions with methylmalonyl-CoA mutase in the rearrangement of methylmalonyl-CoA to succinyl-CoA. A cobalamin deficiency can result in pernicious anemia. Cobalamin is also involved in the reductive conversion of ribonucleotides to deoxyribonucleotides to generate DNA.

In mammals, most of the cellular uptake of cobalamin is regulated by serum transport proteins and by cell membrane receptors. There are two types of cobalamin-binding proteins in plasma: the non-glycosylated protein transcobalamin II (TCII) and the glycosylated proteins transcobalamin I and III (TCI and TCIII), also called R-binder proteins or haptocorrins. TCI and TCIII are immunologically cross-reactive and probably differ only in their carbohydrate composition. TCI is the primary R-binder found in circulation. For simplicity reasons the term TCI will be used when referring to both R-binder proteins TCI and TCIII. Both types of transport proteins (vectors) TCI and TCII circulate in mammalian blood either partly saturated (holo), or partly unsaturated (apo) with cobalamin. A vector-less uptake system for cobalamin with a rather low efficiency in normal cells is also present in mammalian cells (see Sennet, C. and Rosenberg, L. E., Ann. Rev. Biochem. 50, 1053-86 (1981)).

TCII functions in the delivery of plasma cobalamin to all metabolically active cells by receptor mediated endocytosis. It is well known that accelerated cellular proliferation in neoplasia primarily entails increased consumption of cobalamin loaded TCII from circulation by receptor mediated endocytotic uptake. Upregulation in the number of TCII receptors has been widely demonstrated in malignant cell lines to meet the increased metabolic demand of thymidine and methionine production, methylation reactions for DNA synthesis and cellular energetics via mitochondrial metabolism.

The general TCII receptor is present in all tissues while a second and more organ-specific TCII receptor, called megalin, is heavily expressed in kidney proximal tubules and several other absorptive epithelia. After endocytotic internalisation, TCII is degraded in the lysosomes and free cobalamin is transported to the cytoplasm and inside the nuclear membrane, where it is converted into Me-Cbl and Ado-Cbl. These two forms are operating as the active coenzymes of vitamin B12. The essential role of TCII is well established by the observation that inherited inborn lack of TCII leads to megaloblastic anemia, detrimental neurological disorders and death if not treated with excess cobalamin.

Almost all cells are able to generate TCII. Many cells such as hepatocytes, fibroblasts, nervous cells, enterocytes and macrophages synthesize elevated amounts of TCII. It is assumed that the vascular endothelium is the primary source of TCII. Approximately 20-30% of the circulating cobalamin is bound to TCII as holo-TCII. This is the metabolically efficient form that ensures the internalisation of cobalamin in all tissues (see Rothenberg, E. et al., in: Chemistry and Biochemistry of B12, ed. R. Banerjee, New York, N.Y., 1999, pp. 441-473).

TCI is present in blood and plasma as well as in most exocrine secretions and other fluids. It is mainly generated in the foregut tissues, gastric mucosa, salivary and lacrimal glands and secretory epithelium of the inner ear. TCI, unlike TCII, does not seem to deliver its cobalamin primarily for cellular uptake, has a long half-life in the blood, and thus holds more than 75% of circulating cobalamin (and corrin) at any given moment. Almost all TCI circulates as holo-TCI. Its role is not fully understood. It has been proposed to function as a bacteriostatic agent by preventing the supply of all sorts of cobalamins and corrins to microorganisms. It may also stabilise adenosyl-cobalamin and protect if from photolysis. In contrast to TCI, which has a higher concentration than TCII in circulation, the level of TCII can be elevated very quickly by de novo synthesis of apo-TCII in response to incoming cobalamin. TCI is generated rather slowly and can not be stimulated substantially in response to any triggering impact (see Alpers, D. and Russell, G., in: Chemistry and Biochemistry of B12, supra, pp. 411-441).

Until now, the vector-less uptake of cobalamin in mammalian cells has not been considered as an alternative route to supply cobalamin derivatives to hyperproliferative cells. It is undisputed that the physiologically important mechanisms for the uptake of cobalamin by benign mammalian cells requires the vectors TCII and TCI (and intrinsic factor in the digestive tract). However, in vivo and in vitro data show that free cobalamin is also able to traverse the plasma membrane without the involvement of a vector protein. Direct evidence for an additional ability to take up free cobalamin comes from the study of children congenitally and totally deficient in TCII, in whom parenteral administration of free cobalamin resulted in a striking remission of clinical and chemical signs of intracellular cobalamin deficiency (see Hall, C. E. et al., Blood, 53, 251-263 (1979)). In vitro studies showed uptake of free cobalamin in HeLa cells and fibroblasts. In HeLa cells, uptake of free cobalamin is between 1% and 20/of that seen for TCII-bound cobalamin. With human fibroblasts, free cobalamin accumulation in a two-hour interval amounts to about 20% of that noted with TCII-bound vitamin. The free vitamin uptake system in human fibroblasts has been studied in some detail by Berliner and Rosenberg (Berliner, N. and Rosenberg, L. E., Metabolism, 30, 230-236 (1981)). Uptake of free CN-[$^{57}$Co]-Cbl has been established as a biphasic system: The initial uptake component is rapid, saturable and specifically inhibited by excess unlabelled CN-Cbl and OH-Cbl, and complete within 30 min. The second uptake component is slower, linear with time and not inhibited by excess unlabelled cobalamin, and does not plateau even after 8 h, suggesting the characteristic attributes of a non-specific process. The initial mode of uptake has properties of a protein mediated highly specific membrane traversation; it is sensitive to sulfhydryl reagents and markedly inhibited by cycloheximide (Sennet, C. and Rosenberg, L. E., Ann. Rev. Biochem. 50, 1053-86 (1981)). These properties are consistent with the presence of a protein-mediated, facilitated uptake system of free cobalamin in mammals.

It is well established that many bacteria and all eucaryotic protists are auxotrophic for vitamin B12 and able to bind it with higher affinity than mammalian intrinsic factor, TCI and TCII. Bacterial and protozoan B12-binding proteins are vector-less operating cell surface proteins able to bind a wide variety of corrins (including true cobalamin) with high avidity. Therefore, the detection of bacterial infections in the context of a whole body image, following the application of a radio-labelled cobalamin derivative, was no surprise (Collins, D. A. et al., Mayo Clin. Proc. 75, 568-580 (2000)). The development of hyperproliferative forms of mammalian cells may well entail the development by multistep cancerogenesis of more efficient forms of the already present vector-less cobalamin uptake system.

Approaches have been published and patented to use cobalamin as carrier for a broad variety of biologically active agents, including radioactive metal isotopes (see Collins, D. A., U.S. Pat. Appl. No. 2003/0144198). The results obtained in animals and humans, when using radio-labelled cobalamin derivatives, showed labelling of tumour tissues, but also a strong accumulation of radioactivity in healthy tissues, such as kidney and liver. Therefore, imaging and radiotherapy are far from being optimal. The potential for major damages to some healthy parts of the body limits the applications described so far.

There is an obvious need for compounds, compositions and methods to administer diagnostic and therapeutic cobalamin derivatives to rapidly proliferating cells in higher concentrations compared to normal cells. It is the objective of the present invention to provide new methods to identify, synthesise, characterise and apply cobalamin derivatives with higher specificity for cells with abnormally high proliferation, while avoiding the development of resistant cellular off-spring.

SUMMARY OF THE INVENTION

The present invention is based on the observation that, in contrast to cobalamin itself, cobalamin derivatives with no or much reduced binding to the transport protein transcobalamin II (TCII), if properly applied, have a much reduced accumulation rate in blood and benign organs, such as kidney and liver, compared to the accumulation rate in neoplastic tissues, and are more rapidly eliminated from blood. By selecting cobalamin derivatives acting as vitamin B12 substitutes, the risk of the formation of resistant off-spring in neoplastic tissue is much reduced.

The invention relates to cobalamin derivatives (a) having no binding affinity or low binding affinity to transcobalamin II and (b) retaining activity as a vitamin B12 substitute.

In particular the invention relates to cobalamin derivatives (a) having less than 20%, preferably less than 5%, of binding affinity to transcobalamin II when compared to the binding affinity of non-modified cobalamin in a binding test, and (b) retaining more than 2% of the activity as a vitamin B12 substitute in a growth assay.

Examples of compounds of the invention with low or no binding affinity for TCII are specific cobalamin derivatives carrying a therapeutic and/or diagnostic agent, such as a radioactive metal. The compounds of the invention are selected on the basis of the results of a binding test with purified TCII and a growth assay using *Lactobacillus delbrueckii* as the test organism.

The invention further relates to a method of diagnosis of a neoplastic disease or an infection by microorganisms in a mammal comprising (a) exposing the mammal suspected of being inflicted by a neoplastic disease or an infection to a period of a vitamin B12—free diet, and (b) subsequently applying a cobalamin derivative of the invention carrying a diagnostic agent.

The invention likewise relates to a method of treatment of a mammal suffering from a neoplastic disease or an infection by microorganisms comprising (a) exposing the mammal in need of treatment to a period of a vitamin B12—free diet, and (b) subsequently applying a cobalamin derivative of the invention carrying a therapeutic agent.

The invention also relates to the use of a cobalamin derivative according to the invention in a method of diagnosis of a neoplastic disease or an infection by microorganisms or in a method of treatment of a mammal suffering from a neoplastic disease or an infection by microorganisms.

The invention further relates to pharmaceutical compositions comprising cobalamin derivatives of the invention, in particular pharmaceutical compositions suitable for diagnostic applications and pharmaceutical compositions suitable for therapeutic applications, and to the use of such pharmaceutical compositions in a method of diagnosis and in a method of therapeutic treatment, respectively.

The invention also relates to intermediates for the preparation of compounds useful in a diagnostic or therapeutic treatment according the invention, in particular to compounds substituted with chelators for binding radioactive metals, but having no metal or a non-radioactive metal bound to the chelator.

Cobalamin derivatives according to the invention are of particularly high value for the diagnosis and/or the treatment of aggressive, rapidly progressing neoplastic diseases such as cancers and/or diagnosis and/or treatment of local infections by pathogenic microorganisms.

A) Gelfiltration analysis of the radioactive labelled derivative on a Superdex™ 75 column (Peak elutes at 1.5 kDa)

B) Gelfiltration analysis of the derivative mixed with TCI (shift of the peak from 1.5 kDa to 44 kDa)

C) Gelfiltration analysis of the derivative mixed with TCII (peak elutes at 1.5 kDa indicating that cyanocobalamin-b-propyl-PAMA-OEt is essentially a TCII-non binder)

Figure 2:
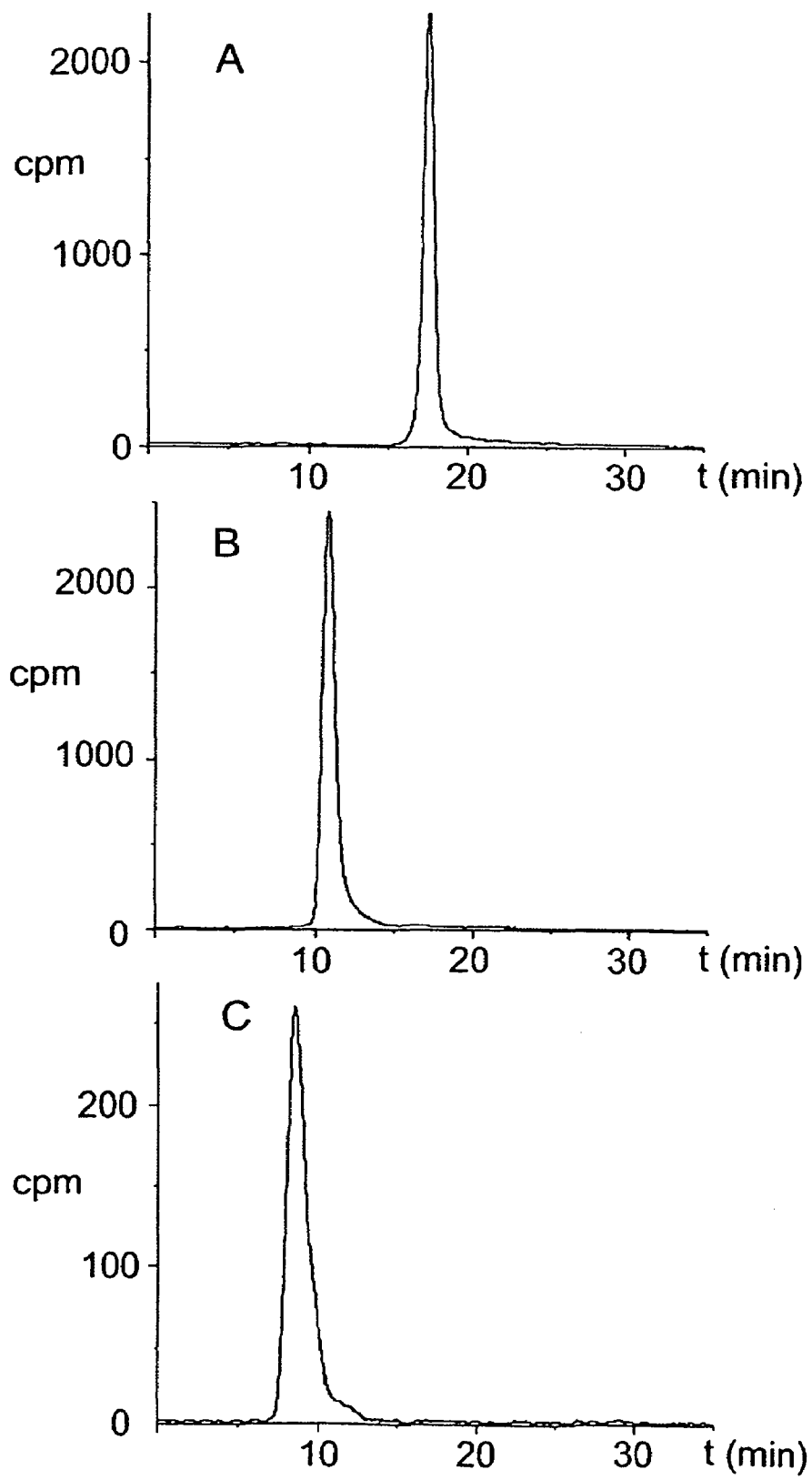

FIG. 2 is a graph illustrating the interaction of radioactive labelled cyanocobalamin-b-butyl-PAPAcet of Example 5, a TCII-binder, with transport proteins in a gel shift assay. t=time, cpm=counts per minute.

A) Gelfiltration analysis of the radioactive labelled derivative on a Superdex™ 75 column (peak elutes at 1.5 kDa)

B) Gelfiltration analysis of the derivative mixed with TCI (shift of the peak from 1.5 kDa to 44 kDa)

C) Gelfiltration analysis of the derivative mixed with TCII (shift of the peak from 1.5 kDa to 60 kDa indicating that cyanocobalamin-b-butyl-PAPAcet does bind to TCII)

FIGS. 3, 4, 5 and 6: Bar graphs illustrating tissue distribution y-axis: percent of the injected radioactivity per gram of tissue x-axis: Organs 1) Blood, 2) Heart, 3) Spleen, 4) Kidney, 5) Stomach, 6) Intestine, 7) Liver, 8) Muscle, 9) Bone, 10) Tumor FIG. 3: Tissue distribution after i.v. injection of radioactive cyanocobalamin ($^{57}$Co—CN-Cbl) in mice fed with normal food.

Figure 4:
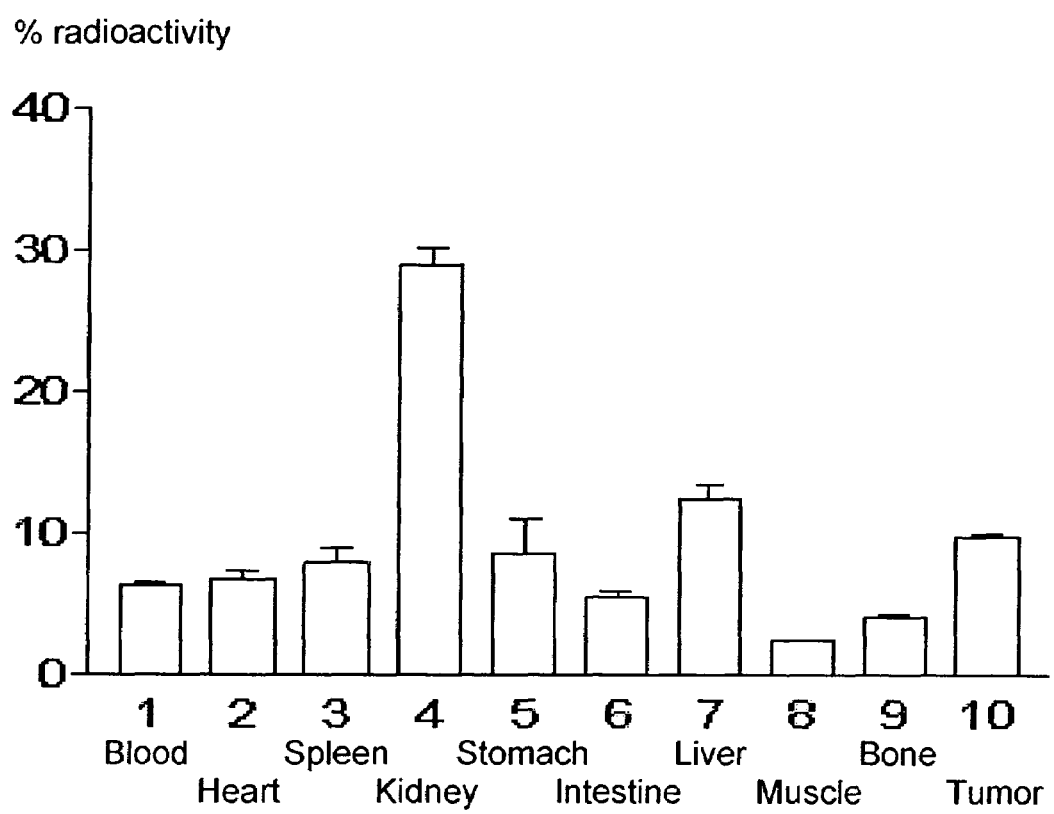

FIG. 4: Tissue distribution after i.v. injection of radioactive cyanocobalamin ($^{57}$Co—CN-Cbl) in mice fed with Vitamin B12 deficient food.

Figure 5:
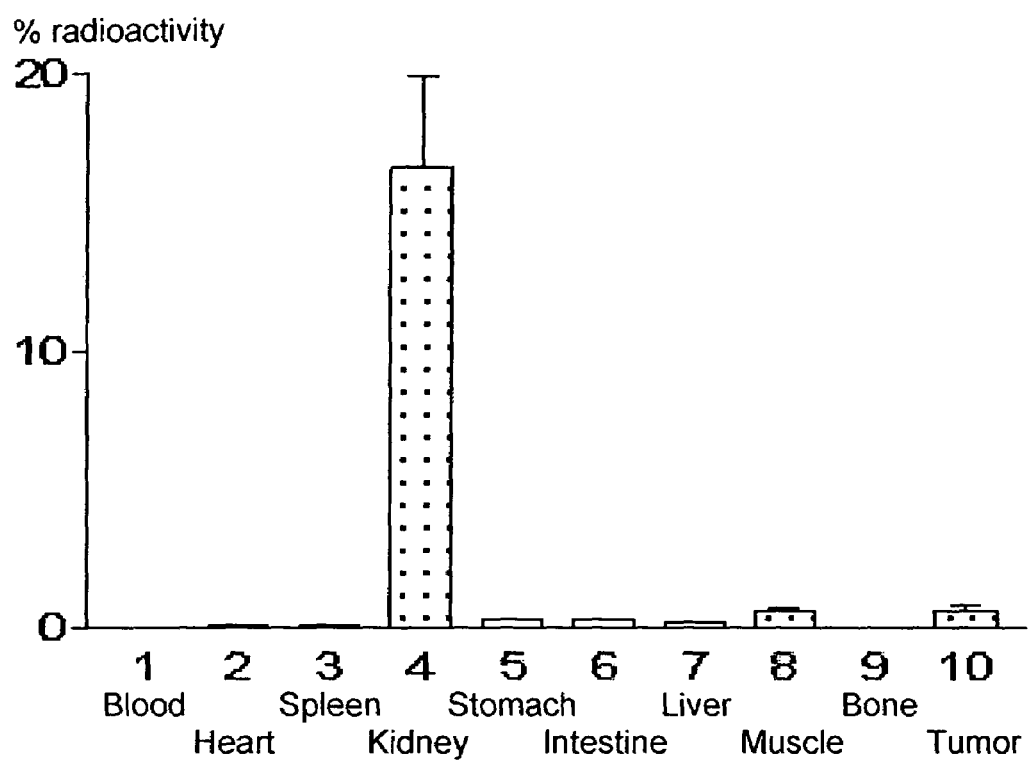

FIG. 5: Tissue distribution after i.v. injection of radioactive cyanocobalamin-b-propyl-PAMA-OEt (Example 11) in mice fed with normal food.

Figure 6:
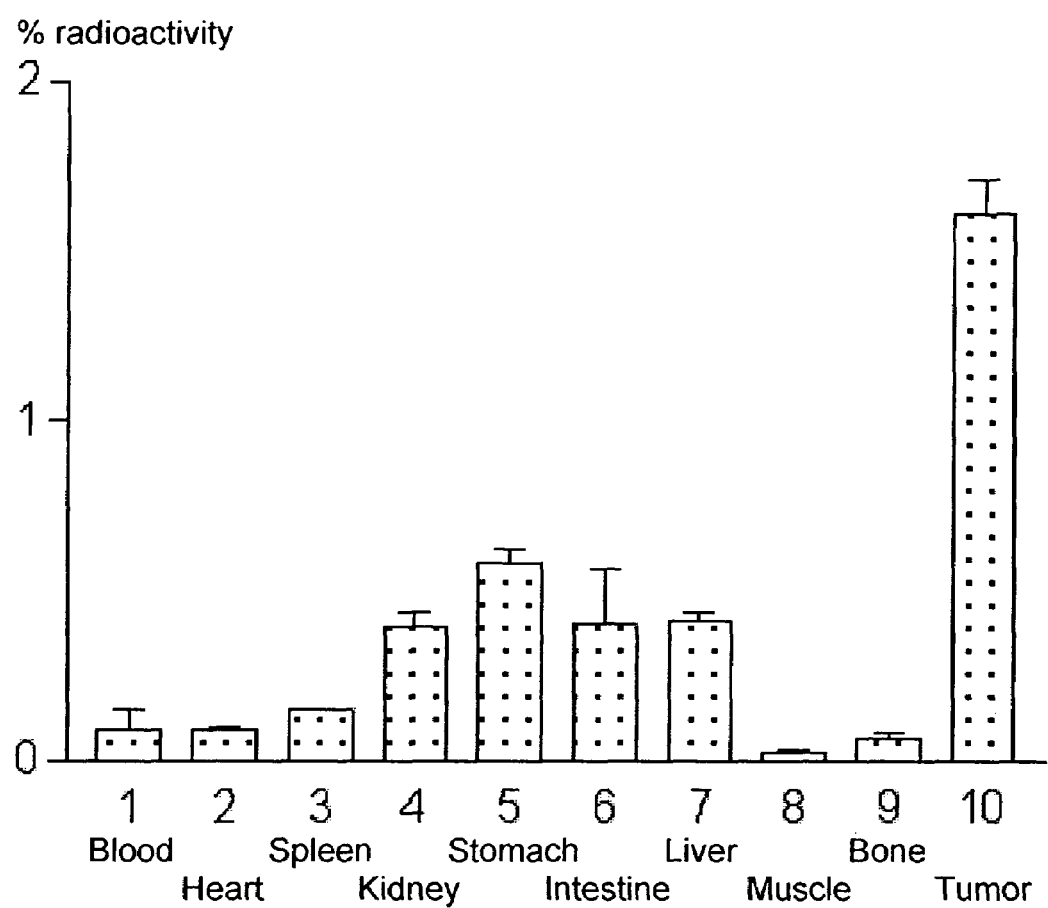

FIG. 6: Tissue distribution after i.v. injection of radioactive cyanocobalamin-b-propyl-PAMA-OEt (Example 11) in mice fed with Vitamin B12 deficient food.

DETAILED DESCRIPTION OF THE INVENTION

Cobalamin derivatives with no or very low binding affinity to the cobalamin vector protein (or transport protein) TCII, when applied to mammals exposed to vitamin B12 diet, exhibit a much reduced accumulation in blood and in crucial organs, such as kidney and liver, while maintaining high uptake rates in hyperproliferative cells and, thus, enabling more precise diagnosis and therapy of neoplastic diseases and of local infections by microorganisms.

Compounds of the invention that have low binding affinity to TCII and retain vitamin B12 activity are e.g. compounds of formula (I)

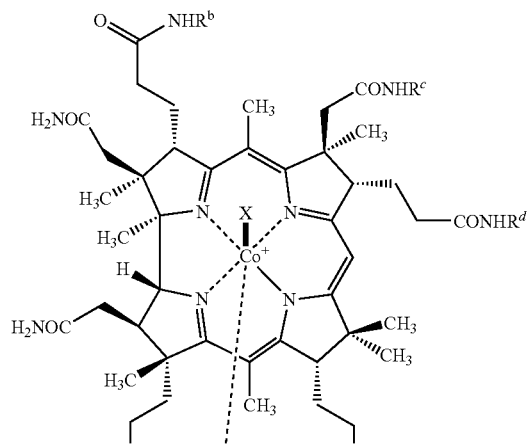

(I)

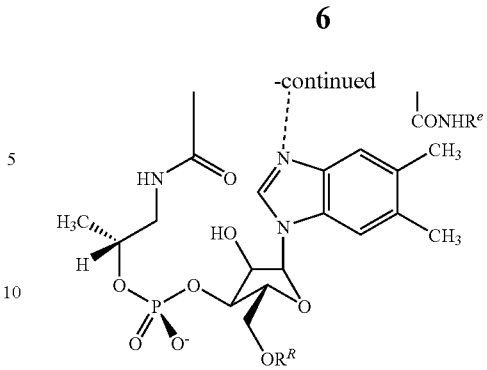

-continued wherein $R^b$, $R^c$, $R^d$ and $R^e$, independently of each other, are a spacer-chelator group, an antibiotic or antiproliferative therapeutic agent, a sterically demanding organic group with 4 to 20 carbon atoms, or hydrogen;

$R^R$ is a spacer-chelator group or an antibiotic or antiproliferative therapeutic agent, each connected through a linker Z, or hydrogen;

with the proviso that at least three of the residues $R^b$, $R^c$, $R^d$, $R^e$ and $R^R$ are hydrogen and at least one of the residues $R^b$, $R^c$, $R^d$ and $R^e$ is different from hydrogen;

X is a monodentate ligand; and the central cobalt (Co) atom is optionally in the form of a radioactive isotope.

In a particular embodiment $R^e$ is hydrogen.

A monodentate ligand X is e.g. cyano;

halogen, such as fluoro, chloro, bromo or iodo, cyanato, isocyanato, thiocyanato, or isothiocyanato;

alkyl, linear or branched and comprising 1 to 25 carbon atoms, preferably 1 to 4 carbon atoms, such as methyl, ethyl, n-propyl, n-butyl or isobutyl, or also n-hexyl or n-decyl, and optionally substituted by hydroxy, methoxy or amino, for example hydroxymethyl, methoxymethyl, aminomethyl, hydroxyethyl or methoxyethyl;

a nitrile R—CN, an isonitrile R—NC, a carboxylate R—COO$^-$ or a thiolate R—S$^-$, wherein R is alkyl, linear or branched and comprising 1 to 15 carbon atoms, preferably 1 to 6 carbon atoms, or aryl, for example phenyl or naphthyl, such as acetonitrile, propionitrile, benzonitrile, methyl isocyanide, phenyl isocyanide, acetate, propionate, benzoate, methylthiolate, ethylthiolate, n-hexylthiolate or thiophenolate;

a phosphite (RO)$_3$P wherein the substituents R are identical or different and represent alkyl comprising 1 to 6 carbon atoms or aryl, for example optionally substituted phenyl or naphthyl, such as trimethylphosphite, methyldiphenylphosphite, triphenyl phosphite or tri-o-tolylphosphite;

hydroxy or aquo; or a 5'-deoxyadenosyl group or a related nucleoside.

Preferably, X is cyano, methyl, hydroxy, aquo or a 5'-deoxyadenosyl group. Most preferred is cyano.

A spacer-chelator group as a substituent $R^b$, $R^c$, $R^d$, $R^e$ or $R^R$ is a chelator for metal atoms attached to the NH or O function of the cobalamin via a spacer, and optionally carries a metal atom, in particular a radioactive metal atom.

Compounds of formula (I) in which the spacer-chelator group does not carry a metal atom are intermediates to be used in the manufacture of compounds useful in a method of diagnostic and/or therapeutic treatment according to the invention.

An antibiotic or an antiproliferative therapeutic agent as a substituent $R^b$, $R^c$, $R^d$, $R^e$ or $R^R$ is a an antibiotic agent selected from aminoglycoside antibiotics, such as gentamycin, tetracyclins, antimetabolites, such as selenomethionin, macrolides, such as erythromycin, and trimethoprim, or an antiproliferative agent selected from antimetabolites, such as 5-fluorouracil, alkylating agent, such as oxaliplatin, dacarbazin, cyclophosphamide or carboplatin, a cell-cycle inhibitor, such as vinblastine or docetaxel, a DNA breaker (topoisomerase inhibitor, intercalator, strand breaker), such as doxorubicin, bleomycin or topotecan, a compound interfering with the signal transduction pathway, such as a caspase activity modifier, agonist or antagonist of cell death receptors, and a modifier of nucleases, phosphatases and kinases, such as imatinib mesylate, dexamethasone, phorbol myristate acetate, cyclosporin A, quercetin, or tamoxifen, either attached directly to the NH or O function of the cobalamin or linked covalently via a spacer.

A spacer is an aliphatic chain of 2 to 10 carbon atoms, preferably 2 to 6 carbon atoms, e.g. 2 to 5 carbon atoms, wherein one or two carbon atoms may be replaced by nitrogen and/or oxygen atoms and the aliphatic chain may be substituted by hydroxy, oxo or amino. In particular two adjacent carbon atoms may be replaced by an amide function —NH—CO— or an ester function —O—CO—.

Particular spacers connecting the NH or O function of the cobalamin with a chelator are ethylene, propylene, butylene or pentylene groups or such groups wherein one carbon is replaced by oxygen or nitrogen, or wherein one carbon atom is replaced by oxygen or nitrogen and the adjacent carbon atom is substituted by oxo.

A chelator is a compound having two, three or more donor atoms selected from nitrogen, oxygen and sulfur in a distance such as to bind to a metal atom. Particular chelators are tridentate chelators having three metal binding sites comprising N, O and/or S donor atoms in a distance from each other allowing binding of metal atoms. Nitrogen atoms as donor atoms are e.g. part of an aliphatic amine, an aromatic amine or a nitrogen-containing aromatic heterocycle. Oxygen atoms as donor atoms are e.g. alcohols, ethers, esters or carboxy functions. Sulfur atoms as donor atoms are e.g. thioethers or thiols. The donors may be connected e.g. by aliphatic carbon chains or chains comprising amide bonds and/or ether functions, and may be amino acid derivatives, polyethers, and the like.

Preferred chelators are the chelators of formula (II) to (IX). Carboxyl groups may be present as esters which cleave concomitantly with complex formation with a metal atom to yield a coordinating carboxylate group. In such esterified chelators, the ester may be an alkyl ester wherein alkyl is linear or branched and comprises 1 to 25 carbon atoms, optionally one to five carbon atoms being replaced by nitrogen or oxygen, or one or two carbon atoms replaced by sulfur or phosphorus, and which are optionally substituted by phenyl, pyridyl, hydroxy, halogen, cyano, oxo or amino. The ester may also be an aryl or heteroaryl ester wherein aryl or heteroaryl has 3 to 10 carbon atoms and zero, one or two oxygen, zero, one, two or three nitrogen or zero or one sulfur atoms. Such ester residues may be suitably substituted in order to make them cleavable under particular reaction conditions, e.g. as described for esters commonly used as protecting groups for carboxylic acids, see Green, T. W., and Wuts, P. G. M., Protective groups in organic synthesis, Wiley 1999.

Esterified chelators, e.g. esterified by methyl, ethyl or cyanoethyl, are also comprised in the definition of preferred chelators.

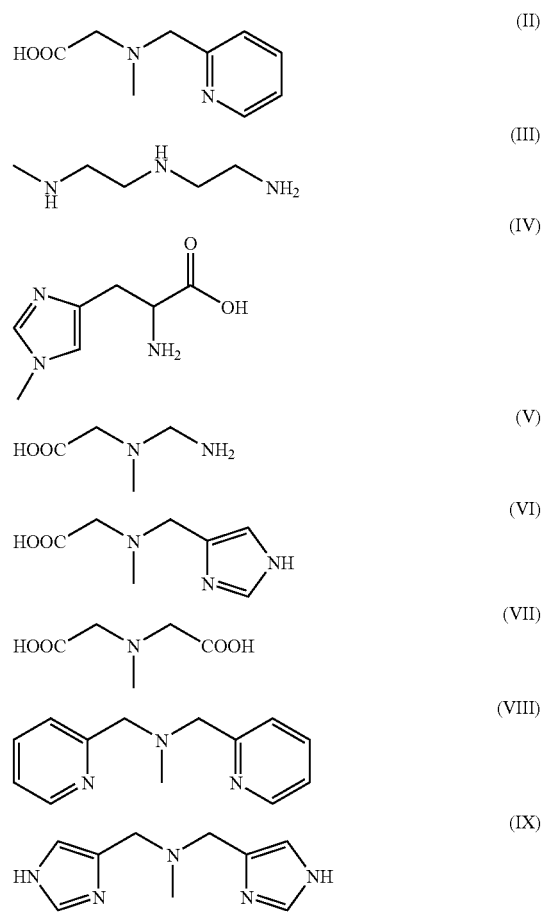

Radioactive metals considered are radioisotopes such as $^{94m}$Tc, $^{99m}$Tc, $^{188}$Re, $^{186}$Re, $^{111}$In, $^{90}$Y, $^{64}$Cu, $^{67}$Cu and $^{177}$Lu, in particular $^{99m}$Tc, $^{188}$Re, $^{186}$Re and $^{111}$In.

Radioactive isotopes of Co considered are e.g. $^{57}$Co and $^{60}$Co.

A sterically demanding organic group with 4 to 20 carbon atoms is e.g. an alkyl, cycloalkyl, aryl, arylalkyl, heteroaryl or heteroarylalkyl group optionally substituted by hydroxy, alkoxy, oxo, amino, carboxy, carbamoyl or alkoxycarbonyl. Examples of aryl groups are phenyl, methylphenyl, dimethylphenyl, hydroxyphenyl or naphthyl. Examples of heteroaryl groups are pyridyl, pyrrolyl, imidazolyl or benzimidazolyl. In an alkyl chain, carbon atoms may be replaced by nitrogen or oxygen atoms. For example, in an alkyl chain, one carbon atom may be replaced by a nitrogen (or oxygen) atom, and the neighbouring carbon atom be substituted by oxo, thereby representing a carboxamide (or ester function, respectively). Particular examples of a sterically demanding organic group are iso-butyl, tert-butyl, tert-pentyl, o-tolyl, o-methylbenzyl, or 2,6-dimethylbenzyl.

A linker Z connecting $R^R$ with a spacer-chelator group or an antibiotic or antiproliferative therapeutic agent is a bond or a linker selected from the group of phosphates, phosphonates, carboxylic esters or alkylene of 1 to 10 carbon atoms and combinations thereof. Such a linker connects the spacer-chelator group or the therapeutic agent optionally comprising a spacer as defined hereinbefore to the oxygen atom of cobalamin.

Compounds that are derivatized at $R^R$ but wherein $R^b$, $R^c$, $R^d$ and $R^e$ are all hydrogen are recognized by the TC's and are still enzymatically active, and therefore excluded from the scope of the invention.

The selection of a compound of the invention is based on the following criteria:

(a) No or very much reduced binding affinity, e.g. less than 20%, in particular less than 10%, preferably less than 5%, more preferably less than 2% binding affinity, to TCII when compared with the binding of (non-modified) cobalamin; and (b) activity as a vitamin B12 substitute in a growth test using a vitamin B12 dependent bacterium or mammalian cell line, e.g. more than 2% activity, in particular more than 10% activity, preferably more than 20% activity when compared to the vitamin B12 activity of (non-modified) cobalamin.

To test the binding affinity of cobalamin (Cbl) derivatives to TCII, an in vitro test is carried out with partially purified TCII obtained from the blood of rabbits. Recombinant TCII produced with an *E. coli* expression system can also be used as a substrate.

Cobalamin derivatives of the invention have to maintain their function as vitamin B12 substitutes. As a result, the risk of resistance development leading to cells with high proliferation rates will be very much reduced. With all likelihood, mutant cells which are no longer able to take up cobalamin derivatives with low or no binding activity to TCII will have lost the advantage of their predecessor cells to achieve high proliferation rates thanks to a highly efficient TCII independent vitamin B12 uptake mechanism.

To test for vitamin B12 activity of a cobalamin derivative an assay is carried out by using *Lactobacillus delbrueckii*, an internationally recommended test strain for cyanocobalamin (CN-Cbl). Supplementation of cyanocobalamin to a cyanocobalamin-free assay medium results in a growth response of the cyanocobalamin-auxotrophic bacterial strain which can be measured by a quantitative solid diffusion plate assay. The test is used to determine to what extent (in %) the cobalamin derivative is able to replace cyanocobalamin as a life supporting catalyst.

The invention relates to a method of diagnosis and a method of treatment of neoplastic diseases and of local infections by microorganisms in a mammal comprising (a) exposing the mammal to a period of a vitamin B12-free diet (b) subsequently applying a cobalamin derivative of the invention carrying a diagnostic or a therapeutic agent, and to the use of the cobalamin derivatives of the invention in such a method.

The positive effect of applying TCII non-binding cyanocobalamin derivatives on their biodistribution in mammals exposed to a vitamin-free diet is illustrated in Table 1.

Example 5 : Cyanocobalamin-b-butyl-PAPAcet
Example 6 : Cyanocobalamin-b-butyl-aminocarboxymethyl-His-OMe
Example 8 : Cyanocobalamin-c-butyl-PAPAcet
Example 10 : Cyanocobalamin-b-ethyl-PAMA-OEt
Example 11 : Cyanocobalamin-b-propyl-PAMA-OEt
Example 12 : Cyanocobalamin-b-butyl-PAMA-OEt
Example 14 : Cyanocobalamin-b-hexyl-PAMA-OEt
Example 18 : Cyanocobalamin-d-propyl-PAMA-OEt
Example 20 : Cyanocobalamin-b-propyl-His-OMe
Example 22 : Cyanocobalamin-b-ethyl-Triamine
Example 25 : Cyanocobalamin-5'-phosphocolamin-His-OMe The results of biodistribution analysis collected in Table 1 indicate that TCII non-binders, e.g. the compounds of the invention as described in Examples 10, 11, 12, 18 and 22, have a comparatively high accumulation in tumor, five times or more than in blood and at least half the amount found in the critical organs kidney and liver. The compounds of the Examples 5, 6, 8, 14, 20 and 25 do not fall under the definition of compounds of the invention since they bind to TCII, and are described here only as reference compounds.

Cobalamin derivatives according to the invention are of particularly high value for the diagnosis and/or the treatment of aggressive, rapidly progressing neoplastic diseases such as cancers. Compounds of the invention can be used for the treatment of highly proliferative cells of human origin involved in malignancies such as melanoma, fibrosarcoma, ovarial carcinoma, pancreas carcinoma, osteosarcoma and acute leukaemia, to mention just a few examples, and are able to bypass TCII mediated endocytosis. The method of the invention allows a specific protection of benign organs from TCII mediated detrimental uptake of cobalamin derivatives carrying a radioactive isotope or/and carrying a non-radioactive agent destroying cells.

Compounds of the invention are not only useful in cancer imaging and cancer therapy, but also for the visualization and the potential treatment of local infections by microorganisms depending on a high and direct uptake of cobalamins.

Compounds of the invention carrying an antiproliferative agent are useful for transporting the agent in an inactive form in to the hyperproliferative cells where it can exert its action after intracellular amidolysis.

In a method of treatment of a neoplastic and/or infectious disease, a compound of the invention carrying a suitable therapeutic agent can be administered alone or in combination with one or more other therapeutic agents, possible combination therapy taking the form of fixed combinations, or the administration of a compound of the invention and one or more other therapeutic agents being staggered or given independently of one another, or the combined administration of fixed combinations and one or more other therapeutic agents. A compound of the invention can, besides or in addition, be

TABLE 1

Tissue distribution 24 h after i.v. injection of radioactive labeled derivatives in mice

| | Example | | | | | | | | | | |
|---|---|---|---|---|---|---|---|---|---|---|---|
| | 5 | 6 | 8 | 10 | 11 | 12 | 14 | 18 | 20 | 22 | 25 |
| TC II reactivity | + | + | + | − | − | − | + | − | + | − | + |
| Blood | 2.30 | 2.40 | 2.20 | 0.10 | 0.09 | 0.04 | 1.20 | 0.06 | 2.10 | 0.25 | 0.18 |
| Kidney | 14.10 | 15.80 | 16.50 | 1.36 | 0.39 | 1.08 | 40.00 | 10.40 | 19.90 | 3.54 | 116.00 |
| Liver | 9.40 | 7.40 | 8.10 | 1.45 | 0.44 | 0.94 | 8.00 | 3.90 | 21.06 | 3.90 | 20.70 |
| Tumor | 7.90 | 7.30 | 3.60 | 0.73 | 1.61 | 6.13 | 3.00 | 6.80 | 9.20 | 2.90 | 3.16 | administered especially for tumor therapy in combination with chemotherapy, immunotherapy, surgical intervention, or a combination of these. Long-term therapy is equally possible as is adjuvant therapy in the context of other treatment strategies.

The invention further relates to pharmaceutical compositions comprising cobalamin derivatives of the invention, in particular pharmaceutical compositions suitable for diagnostic applications and pharmaceutical compositions suitable for therapeutic applications.

Preferred are pharmaceutical compositions for parenteral administration, such as intravenous, intramuscular or subcutaneous administration. The compositions comprise the active ingredient alone or together with a pharmaceutically acceptable carrier. The dosage of the active ingredient depends upon the disease to be treated and upon the species, its age, weight, and individual condition, the individual pharmacokinetic data, and the mode of administration.

Methods of Manufacture

Compounds of the invention are prepared by standard methods known in the art.

Preferably, cyanocobalamin, i.e. the compound of formula (I) wherein $R^b$, $R^c$, $R^d$, $R^e$ and $R^R$ are hydrogen and X is cyano, is hydrolyzed under controlled conditions, e.g. with dilute mineral acid, and the obtained mixture of mono-acids, wherein one of the carbamoyl groups $CONH_2$ is converted to COOH, separated. Bis-acids may be obtained similarly.

Cyanocobalamin-b, c, d or e-acid, i.e. the compound of formula (I) wherein $CONHR^b$, $CONHR^c$, $CONHR^d$ or $CONHR^e$ is replaced by COOH, respectively, and X is cyano, may then be reacted with a corresponding amine $R^b$—$NH_2$, $R^c$—$NH_2$, $R^d$—$NH_2$ and $R^e$—$NH_2$, respectively, under standard conditions for amide formation, e.g. as known in the chemistry of peptides. Functional groups in residues $R^b$, $R^c$, $R^d$ and $R^e$ that interfere with amide formation are preferably in protected form, and are deprotected by standard methods after amide formation. For the preparation of compounds wherein the spacer comprises an amide function, it is also possible to react cyanocobalamin-b, c, d or e-acid with a diamine $H_2N(CH_2)_nNH_2$ under amide-forming standard conditions, and to further condense the $H_2N(CH_2)_n$-functionalized cyanocobalamin obtained with a corresponding carboxylic acid again under amide-forming standard conditions to generate the substituent $R^b$, $R^c$, $R^d$ and $R^e$, respectively.

For the preparation of compounds wherein $R^c$ is different from hydrogen, the preferred method is formation of the o-lactone followed by a reductive lactone ring opening reaction according to Brown et al., Inorg. Chem. 1995, 3038.

For the preparation of compounds wherein $R^R$ is different from hydrogen, cyanocobalamin (or a cyanocobalamin derivative wherein $R^b$, $R^c$, $R^d$ or $R^e$ is different from hydrogen) is reacted with $R^R$-L wherein L is a suitable activating leaving group for forming an ester bond, e.g. halogen, the residue of a mixed anhydride or another of the usual activating residues for carboxylic, phosphate or phosphonate ester formation customary in peptide and nucleic acid synthesis.

The following Examples serve to illustrate the invention without limiting the invention in its scope.

EXAMPLES

Reagent grade chemicals were from Merck, Dietikon (CH), Aldrich or Fluka, Buchs (CH) and were used without further purification.

BOP=1-benzotriazolyloxy tris(dimethylamino)phosphonium hexafluorophosphate
DCC=dicyclohexylcarbodiimide
DIPEA=diisopropylethylamine
EDC=1-ethyl-3-(3dimethylaminopropyl)carbodiimide
Fmoc=(9H-fluoren-9-ylmethoxy)carbonyl
HOSu=N-hydroxysuccinimide
MES=2-(4-morpholinyl)ethanesulfonic acid
RT=room temperature
TBTU=benzotriazol-1-yl-N-tetramethyluronium tetrafluoroborate
TEAP=Triethylammonium phosphate
Teoc=2-trimethlysilyl-ethoxycarbonyl
TFA=trifluoroacetic acid HPLC analyses were performed on a Merck-Hitachi L-7000 system equipped with a EG&G Berthold LB 508 radiometric detector, using Waters XTerra RP8 columns (5 μm particle size, 1×100 mm) and a flow rate of 1 ml/min. Chromatograms were recorded at 250 and 360 nm. Solvent a were predominantly aqueous buffers. Sodium acetate buffer a was prepared by mixing 2.9 ml acetic acid and 4.55 ml sodium hydroxide 2 M in 900 ml water and 100 ml methanol. Tris buffer a was prepared by dissolving tris(hydroxymethyl)-aminomethane (605 mg) in water, adding HCl 2 M to reach a pH of 8.2, adjusting the volume to in 1000 ml, and adding acetonitrile (10 ml). Solvent b was always methanol.

Preparative HPLC separations were performed on a Varian Prostar system equipped with two Prostar 215 pumps and a Prostar 320 UV/Vis is detector, using Waters XTerra Prep RP8, columns (5 μm particle size, 3×100 mm and 30×100 mm). Flow rates were 4 ml/min for the 3×100 mm column and 30 ml/min for the 30×100 mm column.

UV/Vis spectra were recorded on a Varian Cary 50 spectrometer, IR spectra were recorded on a Bio-Rad FTS-45 spectrometer with the samples in compressed KBr pills. Electrospray ionisation mass spectra (ESI-MS) were recorded on a Merck Hitachi M-8000 spectrometer. In rhenium compounds, the values of the $^{187}Re$ isotope are reported. NMR spectra were recorded on a Bruker DRX 500 MHz spectrometer. The chemical shifts are reported relative to residual solvent protons as a reference.

Cobalamin derivatives (mg quantities) were desalted by applying an aqueous solution of the compound to a Chromafix RP18ce cartridge, followed by thoroughly rinsing with water. The desalted product was then eluated with methanol, the solvent removed in vacuo, and the product dried at high vacuum. Bigger quantities (above 50 mg) were desalted by phenol extraction as described in Meth. Enzymol. 1971, 18(3), p. 43.

(N-3-Aminopropyl-N-pyridin-2-ylmethyl-amino)acetic acid ethyl ester (propyl-PAMA-OEt) was prepared as described for the pentyl analog by Schibli et al. (Nucl. Med. Biol. 2003, 30, 465). The compound is prone to cyclize under basic conditions. Therefore, the Boc protected intermediate was stored and Boc was removed just prior to further functionalization by stirring in diluted aqueous HCl. The ethyl and hexyl derivatives were prepared in an analogous way.

Re([N-3-aminopropyl-N-pyridin-2-ylmethyl-amino]acetic acid)(CO)$_3$ was prepared by reacting fully deprotected (N-3-aminopropyl-N-pyridin-2-ylmethyl-amino)acetic acid with (NEt$_4$)$_2$[Re(OH$_2$)$_3$(CO)$_3$].

Methyl 1-carboxymethyl-N-Fmoc-histidinate trifluoroacetate was prepared as described by Pak et al. (Chem. Eur. J. 2003, 9, 2053-2061). The counter ion is exchanged to chloride by stirring the compound in HCl 0.05 M, followed by evaporation in vacuo at room temperature.

Methyl 3-aminopropyl-N-Teoc-histidinate was prepared as described by van Staveren et al. (Organic & Molecular Chemistry 2004, 2, 2593).

3-(N-2-Cyanoethoxycarbonylmethyl)-N-pyridin-2-ylmethyl-amino)propionic acid 4-nitro-phenyl ester was prepared as described by Kunze (Dissertation, University of Zürich, 2004).

Example 1

Cyanocobalamin Monocarboxylic Acids (b, d and e)

Vitamin B12 (1.88 g, 1.39 mmol) is hydrolyzed in HCl 0.1 M (190 ml) as described by Pathare et al. (Bioconjugate Chem. 1996, 217). The purification is modified in the following way: The Dowex column allows, after desalting by phenol extractions, the isolation of three fractions, one containing exclusively d-acid, a second one containing exclusively b-acid and d-acid, a third one exclusively b-acid and e-acid. The mixture of b-acid and d-acid is separated by preparative HPLC (column: Waters XTerra Prep RP8, 5 µm, 30×100 mm; gradient a/b 0.5% min$^{-1}$ starting from 100% acetate buffer a). The mixture of b-acid and e-acid is separated on the same system but using the Tris buffer as solvent a. Cyanocobalamin-b-acid is isolated in a yield of 280.6 mg (4.9%), cyanocobalamin-d-acid in a yield of 131.5 mg (7.0%), and cyanocobalamin-e-acid in a yield of 94.26 mg (5.0%).

Example 2

Cyanocobalamin-b-(2-aminoethyl)amide[cyanocobalamin-b-ethylamine]

Cyanocobalamin-b-(2-aminoethyl)amide was prepared as described by Pathare et al. (Bioconjugate Chem. 1996, 217) for the synthesis of the dodecane analog. Ethylene diamine (132 mg; 0.147 ml; 2.2 mmol) was dissolved in a DMF/H$_2$O mixture (10 ml; 1/1 v/v). The pH was adjusted to 5 by addition of 1 M HCl. To the solution were added cyanocobalamin-b-acid (60.0 mg, 44.4 µmol) and KCN (57 mg; 0.87 mmol), followed by adjustment of the pH to 5.5. Next, EDC (84.2 mg; 0.43 mmol) and HOSu (50.6 mg; 0.44 mmol) were added. The mixture was stirred at RT for 3 days, and extra portions of EDC and HOSu were added at 24 h intervals. For the workup, the mixture was evaporated to dryness in vacuo, followed by preparative HPLC purification (acetate system, gradient: 0.5% min$^{-1}$ starting from 100% buffer a) to afford 34 mg (55%) of cyanocobalamin-b-(2-aminoethyl)amide.

MS (MeOH; ESI-pos.): m/z=1398.8 [M+H]$^+$, 1420.1 [M+Na]$^+$, 699.4 [M+H]$^{2+}$, 711.1 [M+H+Na]$^{2+}$.

Example 3

Cyanocobalamin-b-(4-aminobutyl)amide[cyanocobalamin-b-butylamine]

was prepared as described above for the synthesis of the ethyl analog.

MS (MeOH, ESI-pos.): m/z=1427.1 [M+1]$^+$, 714.5 [M+3]$^{2+}$.

Example 4

Cyanocobalamin-b-ethyl-PAPAcet

Cyanocobalamin-b-ethylamine (Example 2; 24 mg; 17.2 µmol) was dissolved in a DMF/DMSO mixture (5 ml; 4/1 v/v). To this mixture was added 3-[N-2-cyanoethoxy-carbonylmethyl-N-pyridin-2-ylmethyl-amino]-propionic acid 4-nitrophenyl ester (14 mg, 34.1 µmol) and DIPEA (5 µl, 29 µmol). After stirring at RT for 24 h, the mixture was evaporated to dryness in vacuo. Purification by preparative HPLC (acetate system, gradient: 0.5% min$^{-1}$ starting from 100% buffer a) afforded 20 mg (70%) cyanocobalamin-b-ethyl-PAPAcet as a red solid.

MS (MeOH; ESI-pos.): m/z=1672.1 [M+H]$^+$, 836.9 [M+H]$^{2+}$.

Example 5

Cyanocobalamin-b-butyl-PAPAcet

Cyanocobalamin-b-butylamine (Example 3, 5.5 mg, 3.9 µmol) and 3-[N-2-cyanoethoxy-carbonylmethyl-N-pyridin-2-ylmethyl-amino]propionic acid 4-nitrophenyl ester (2.5 mg, 6.1 µmol) were dissolved in a mixture of dry DMSO (0.5 ml) and DMF (0.5 ml). DIPEA (5 µl, 29 µmol) was added to reach a pH between 8 and 9, and the mixture was stirred at room temperature. After 5 h, HPLC analysis confirmed complete product formation. The solvent was partially evaporated in vacuo to allow the product to precipitate upon addition of ethyl ether. The suspension was centrifugated and decanted three times to give a fine powder. Purification by preparative HPLC (acetate system, gradient: 0.5% min$^{-1}$ starting from 100% buffer a) gave the pure product in an yield of 2.7 mg (41%).

ESI-MS: m/z=850.1 [M+2]$^{2+}$ UV/Vis: λ/nm (ε/mol l$^{-1}$ cm$^{-1}$)=279.1 (17300), 361.0 (31200), 519.9 (8700), 552.0 (9700).

Example 6

Cyanocobalamin-b-butyl-aminocarboxymethyl-His-OMe

A solution of cyanocobalamin-b-butylamine (49.6 mg, 34.8 µmol) in dry DMSO (2 ml) was added to methyl 1 carboxymethyl-N-Fmoc-histinate hydrochloride (35.5 µmol) and BOP (46.2 mg, 104.4 µmol). DIPEA (12 µl, 70.0 µmol) was added, and the solution was stirred at RT for 16 h. HPLC analysis confirmed full conversion of the cobalamin starting material into the Fmoc protected intermediate. The intermediate was precipitated by adding diethyl ether, and the suspension was centrifugated and decanted trice to give a fine powder. The intermediate was dissolved in DMF (5 ml), and piperidine (225 µl) was added. After stirring at RT for 1.5 h, the product was precipitated by adding diethyl ether, and the suspension was centrifugated and decanted three times to give a fine powder. Purification by preparative HPLC (acetate system, gradient: 1% min$^{-1}$ starting from 100% buffer a) gave the pure product in a yield of 17.1 mg (32.1%).

UV/Vis: λ/nm (ε/mol l$^{-1}$cm$^{-1}$)=279.1 (19200), 361.0 (24700), 521.0 (9600), 551.1 (10700).

Example 7

Cyanocobalamin-c-(4-aminobutyl)-amide[cyanocobalamin-c-butylamine]

Cyanocobalamin-c-acid was prepared as described by Brown et al. (Inorg. Chem. 1995, 3038). 1,4-Diaminobutane (0.059 ml; 0.59 mmol) was dissolved in a DMF/H$_2$O mixture (10 ml; 1/1 v/v). The pH was adjusted to 5.2 by addition of 1 M HCl. To the solution were added cyanocobalamin-c-acid (16.0 mg, 11.8 µmol), KCN (15.3 mg; 0.236 mmol), EDC (9.0 mg; 47.2 µmol) and HOSu (5.4 mg; 47.2 µmol). The mixture was stirred at RT for 4 days, and extra portions of EDC and HOSu were added. After another day, extra portions of EDC and HOSu were added again. After a total of 6 days, HPLC analysis confirmed complete conversion of the cobalamin derivative. For the work-up, the mixture was evaporated to dryness in vacuo, followed by preparative HPLC purification (RP C18 column, HCl 1 mM as buffer a, gradient: from 20% methanol to 50% methanol in 30 minutes) to afford 9.8 mg (58%) of cyanocobalamin-c-butylamine.

MS (MeOH; ESI-pos.): m/z=1427.7 $[M+2]^+$, 713.5 $[M+1]^{2+}$.

Example 8

Cyanocobalamin-c-butyl-PAPAcet

Cyanocobalamin-c-butylamine (7.0 mg, 4.9 µmol) and 3-[N-2-cyanoethoxycarbonylmethyl-N-pyridin-2-ylmethyl-amino]propionic acid 4-nitrophenyl ester (3.8 mg, 9.2 µmol) were reacted and purified as described in the synthesis of cyanocobalamin-b-butyl-PAPAcet (Example 5) to give the pure product in an yield of 3.8 mg (78%).

ESI-MS: m/z=1701.0 $[M+1]^+$, 850.1 $[M+1]^{2+}$. UV/Vis: $\lambda$/nm ($\epsilon$/mol l$^{-1}$cm$^{-1}$) 278.1 (14500), 362.1 (25400), 550.0 (7900).

Example 9

Cyanocobalamin-b-butyl-PAPA-Re(CO)$_3$

Cyanocobalamin-b-butylamine (Example 3, 24.6 mg, 17.2 µmol) and Re(CO)$_3$(3-[N-carboxymethyl-N-pyridin-2-ylmethyl-amino]propionic acid) (9.1 mg, 17.2 µmol) were dissolved in DMSO. BOP (22.9 mg, 51.7 µmol) and DIPEA (2.94 µl, 17.2 µmol) were added, and the mixture was stirred at room temperature. DIPEA and BOP were added daily during 4 days. HPLC analysis confirmed formation of two products. They were precipitated upon addition of ethyl ether. The suspension was centrifugated and decanted three times to give a fine powder. Purification by preparative HPLC (acetate system, gradient: 0.5% min$^{-1}$ starting from 100% buffer a) allowed the isolation of the main product peak in a yield of 2.3 mg (7.0%).

ESI-MS: m/z=1917.5 $[M+2]^+$, 959.9 $[M+4]^{4+}$.

Example 10

Cyanocobalamin-b-ethyl-PAMA-OEt

Cyanocobalamin-b-acid (20.0 mg, 14.8 µmol) was dissolved in DMSO (0.8 ml). Subsequently were added DMF (2 ml) and NEt$_3$ (0.1 ml). In a different flask ca. 5 equivalents of (N-2-aminoethyl-N-pyridin-2-ylmethyl-amino)acetic acid ethyl ester (ethyl-PAMA-OEt) hydrochloride (prepared via cleavage of the Boc-protected derivative by stirring in an abs. EtOH/2 M HCl mixture (7.5 ml 4/1 v/v) overnight and subsequent removal of the volatiles in vacuo) was dissolved in a DMF/NEt$_3$ mixture (4.5 ml; 8/1 v/v). The two solutions were mixed, followed by addition of TBTU (32.1 mg, 0.1 mmol). After stirring at RT for 45 min, the solvent was removed in vacuo. The residue was purified by preparative HPLC (acetate system, gradient: 1.0% min$^{-1}$ starting from 100% buffer a) to afford 12 mg (51%) of cyanocobalamin-b-ethyl-PAMA-OEt as a red solid.

MS (MeOH; ESI-pos.): m/z=1575.8 $[M+H]^+$, 788.7 $[M+H]^{2+}$, 799.3 $[M+H+Na]^{2+}$.

Example 11

Cyanocobalamin-b-propyl-PAMA-OEt

A solution of freshly prepared (N-3-aminopropyl-N-pyridin-2-ylmethyl-amino)acetic acid ethyl ester (361 µmol) in water (1 ml) is added to cyanocobalamin-b-acid (65.0 mg, 48.1 µmol). EDC (46.1 mg, 240 µmol) is added, and the pH is adjusted to 5.5 with NaOH 0.1 M. After stirring at RT for 15 h, HPLC analysis (sodium acetate buffer) shows about 50% of product formation. EDC (46.1 mg, 240 µmol) is added again, but prolonged stirring at room temperature does not lead to further product formation. The solvent is removed in vacuo, and the residue is purified by preparative HPLC (gradient a/b 0.5% min$^{-1}$ starting from 100% acetate buffer a). The main fraction is collected, the solvent removed in vacuo, and the product desalted to give cyanocobalamin-b-propyl-PAMA-OEt in a yield of 25.8 mg (16.2 µmol, 33.3%).

ESI-MS: m/z=806.5 $[M+1+Na]^{2+}$, 795.6 $[M+2]^{2+}$. UV/Vis: $\lambda$/nm ($\epsilon$/mol l$^{-1}$cm$^{-1}$)=278.0 (8500), 361.1 (26500), 549.1 (8000).

Example 12

Cyanocobalamin-b-butyl-PAMA-OEt

Cyanocobalamin-b-acid (20.0 mg, 14.8 µmol) was dissolved in DMSO (0.8 ml). Subsequently were added DMF (2 ml) and NEt$_3$ (0.1 ml). In a different flask ca. 5 equivalents of (N-4-aminobutyl-N-pyridin-2-ylmethyl-amino)acetic acid ethyl ester (butyl-PAMA-OEt) hydrochloride (prepared via cleavage of the Boc-protected derivative by stirring in an abs. EtOH/2 M HCl mixture (7.5 ml 4/1 v/v) overnight and subsequent removal of the volatiles in vacuo) was dissolved in a DMF/NEt$_3$ mixture (4.5 ml; 8/1 v/v). The two solutions were mixed, followed by addition of TBTU (32.1 mg, 0.1 mmol). After stirring at RT for 45 min, the solvent was removed in vacuo. The residue was purified by preparative HPLC (acetate system, gradient: 1.0% min$^{-1}$ starting from 100% buffer a) to afford 15 mg (63%) of cyanocobalamin-b-butyl-PAMA-OEt as a red solid.

Example 13

Cyanocobalamin-b-butyl-PAMA-OH

Bromoacetic acid 9H-fluoren-9-ylmethyl ester was prepared from bromoacetyl bromide and 9H-fluorenylmethanol in dry THF at 0° C. Boc-butyl-PAMA-OFm ([(4-tert-butoxycarbonylamino-butyl)-pyridin-2-ylmethyl-amino]-acetic acid 9H-fluoren-9-ylmethyl ester) was prepared from Boc-NH—(CH$_2$)$_4$NH$_2$, pyridine-2-aldehyde and bromoacetic acid 9H-fluoren-9-ylmethyl ester according to the procedure used by Schibli et al. (Nucl. Med. Biol. 2003, 30, 465) for the synthesis of Boc-pentyl-PAMA-OMe.

Cyanocobalamin-b-acid (20.0 mg, 14.8 µmol) was dissolved in DMSO (0.8 ml). Subsequently were added DMF (2 ml) and NEt$_3$ (0.1 ml). In a different flask ca. 5 equivalents of [(4-amino-butyl)-pyridin-2-ylmethyl-amino]-acetic acid 9H-fluoren-9-ylmethyl ester (butyl-PAMA-OFm) (prepared via cleavage of the Boc-protected derivative by stirring in a trifluoroacetic acid/CH$_2$Cl$_2$ mixture (4 ml 1/2 v/v) for 1 hr and subsequent removal of the volatiles in vacuo) was dissolved in a DMF/NEt$_3$ mixture (4.5 ml; 8/1 v/v). The two solutions were mixed, followed by addition of TBTU (32.1 mg, 0.1 mmol). After stirring at RT for 45 min, the solvent was removed in vacuo. The residue was purified by preparative HPLC (acetate system, gradient: 1.5% min$^{-1}$ starting from 100% buffer a) to afford 15 mg of cyanocobalamin-b-butyl-PAMA-OFm as a red solid.

Cyanocobalamin-b-butyl-PAMA-OFm (15 mg) was dissolved in 3 ml of a HNEt$_2$/DMF mixture (2/1 v/v) and stirred at RT for 2 h. The solvent was removed in vacuo, and the residue was purified by preparative HPLC (acetate system, gradient: 1.0% min$^{-1}$ starting from 100% buffer a) to afford 9 mg of cyanocobalamin-b-butyl-PAMA-OH as a red solid.

Example 14

Cyanocobalamin-b-hexyl-PAMA-OEt

Cyanocobalamin-b-acid (20.0 mg, 14.8 µmol) was dissolved in DMSO (0.8 ml). Subsequently were added DMF (2 ml) and NEt$_3$ (0.1 ml). In a different flask ca. 5 equivalents of (N-6-aminohexyl-N-pyridin-2-ylmethyl-amino)acetic acid ethyl ester (hexyl-PAMA-OEt) hydrochloride (prepared via cleavage of the Boc-protected derivative by stirring in an abs. EtOH/2 M HCl mixture (7.5 ml 4/1 v/v) overnight and subsequent removal of the volatiles in vacuo) was dissolved in a DMF/NEt$_3$ mixture (4.5 ml; 8/1 v/v). The two solutions were mixed, followed by addition of TBTU (32.1 mg, 0.1 mmol). After stirring at RT for 45 min, the solvent was removed in vacuo. The residue was purified by preparative HPLC (acetate system, gradient: 1.0% min$^{-1}$ starting from 100% buffer a) to afford 10 mg (41%) of cyanocobalamin-b-hexyl-PAMA-OEt as a red solid.

MS (MeOH, ESI-pos.): m/z=816.9 [M+2H]$^+$, 1632 [M+H]$^+$.

Example 15

Cyanocobalamin-b-ethyl-PAMA-Re(CO)$_3$

Cyanocobalamin-b-ethyl-PAMA-OEt (Example 10, 11 mg; 7.0 µmol) was dissolved in 4 ml of a 2 M NaHCO$_3$ solution. A solution of 11 mg of (NEt$_4$)$_2$[ReBr$_3$(CO)$_3$] (14.2 µmol) in 1.5 ml MeOH was added. The mixture was heated at 85° C. for 1 h. After allowing the mixture to reach RT, it was purified by preparative HPLC (acetate system, gradient: 2.0% per min starting from buffer a). Yield: 11 mg (86%).

Example 16

Cyanocobalamin-b-propyl-PAMA-Re(CO)$_3$

Cyanocobalamin-b-acid (26.7 mg, 19.8 µmol), Re([N-3-aminopropyl-N-pyridin-2-ylmethyl-amino]acetic acid) (CO)$_3$ (29.2 mg, 60 µmol), EDC (11.5 mg, 60 µmol) and HOSu (6.9 mg, 60 µmol) are dissolved in a mixture of water (5 ml) and DMSO (0.5 ml), and the pH is adjusted to 5.5 with dilute HCl and NaOH. After 5 h of stirring at RT, HPLC analysis (acetate buffer) shows about 33% product formation. EDC and HOSu are added again. The mixture is stirred at room temperature for 3 days with addition of EDC and HOSu at 24 h intervals. The water is removed in vacuo, and the product is precipitated by adding diethyl ether. The oily suspension is centrifugated and decanted. Washing with diethyl ether is repeated twice until a fine precipitate forms. The crude product is dried at high vacuum, purified by preparative HPLC (gradient a/b 1% min$^{-1}$ starting from 100% acetate buffer a), and desalted to give cyanocobalamin-b-propyl-PAMA-Re(CO)$_3$ in a yield of 9.1 mg (23%).

ESI-MS: m/z=1831.7 [M+1]$^+$, 916.1 [M+1]$^{2+}$. UV/Vis: λ/nm (ε/mol l$^{-1}$cm$^{-1}$)=278.0, 361.1, 519.9, 551.1.

Example 17

Cyanocobalamin-b-hexyl-PAMA-Re(CO)$_3$

Cyanocobalamin-b-acid (20.0 mg, 14.8 µmol) was dissolved in DMSO (0.8 ml). Subsequently were added DMF (2 ml) and NEt$_3$ (0.1 ml). In a different flask ca. 5 equivalents of [Re([N-3-aminopropyl-N-pyridin-2-ylmethyl-amino]acetic acid) (CO)$_3$].CF$_3$COOH (prepared via Boc cleavage of the protected complex in CH$_2$Cl$_2$ and TFA-(2/1 v/v) for 1 h at 0° C., followed by removal of the volatiles at RT in vacuo) were dissolved in a DMF/NEt$_3$ mixture (4.5 ml; 8/1 v/v). The two solutions were mixed, followed by addition of TBTU (32.1 mg, 0.1 mmol). After stirring at RT for 45 min, the solvent was removed in vacuo. The residue was purified by preparative HPLC (acetate system, gradient: 2.0% min$^{-1}$ starting from 100% buffer a) to afford 11 mg (40%) of cyano-cobalamin-b-hexyl-PAMA-Re(CO)$_3$.

MS (MeOH, ESI-pos.): m/z=936.5 [M+2H]$^{2+}$, 948.3 [M+H+Na]$^{2+}$, 1873.8 [M+H]$^+$.

Example 18

Cyanocobalamin-d-propyl-PAMA-OEt

Cyanocobalamin-d-acid (9.3 mg, 6.9 µmol) was reacted with (N-3-aminopropyl-N-pyridin-2-ylmethyl-amino)acetic acid ethyl ester (7 µmol) and EDC (6.6 mg, 34 µmol) as described for the synthesis of cyanocobalamin-b-propyl-PAMA-OEt (Example 11). The product was isolated in a yield of 3.6 mg (33%)

ESI-MS: m/z=1612 [M+Na]$^+$, 1590 [M+1]$^+$, 806 [M+1+Na]$^{2+}$, 795.1 [M+2]$^{2+}$. UV/Vis: λ/nm (ε/mol l$^{-1}$cm$^{-1}$)=279.0 (13400), 361.1 (23300), 549.1 (7200).

Example 19

Cyanocobalamin-d-propyl-PAMA-Re(CO)$_3$

Cyanocobalamin-d-acid (20.0 mg, 14.8 µmol) was dissolved in DMSO (1.5 ml). Subsequently were added DMF (2 ml) and NEt$_3$ (0.1 ml). In a different flask ca. 5 equivalents of Re([N-3-aminopropyl-N-pyridin-2-ylmethyl-amino]acetic acid)(CO)$_3$ were dissolved in a DMF/NEt$_3$ mixture (4.5 ml; 8/1 v/v). The two solutions were mixed, followed by addition of TBTU (32.1 mg, 0.1 mmol). After stirring at RT for 45 min, the solvent was removed in vacuo. The residue was purified by preparative HPLC (acetate system, gradient: 2.0% min$^{-1}$ starting from 100% buffer a) to afford 20 mg (73%) of cyano-cobalamin-d-propyl-PAMA-Re(CO)$_3$.

Example 20

Cyanocobalamin-b-propyl-His-OMe

Cyanocobalamin-b-acid (20.0 mg, 14.8 µmol) was dissolved in DMSO (0.8 ml). Subsequently were added DMF (2 ml) and NEt$_3$ (1 ml). In a different flask about 4 equivalents of methyl 3-aminopropyl-N-Teoc-histidinate were dissolved in DMF. The mixtures were added together, and TBTU (32.1 mg; 0.1 mmol) was added. The mixture was stirred for 45 min, and subsequently evaporated to dryness in vacuo. Purification by preparative HPLC (acetate system; gradient: 2.0% per min, starting from buffer a) afforded 16 mg of a red solid. (67%).

MS (MeOH; ESI-pos.): m/z=1710.4 [M+H]$^+$, 855.0 [M+2H]$^{2+}$, 866.7 [M+Na+H]$^{2+}$.

A 19 mg sample of this Teoc-protected compound was dissolved in a TFA/CH$_2$Cl$_2$ mixture (4/1 v/v) at 0° C. After stirring for 4 h at this temperature, analytical HPLC showed full conversion of the starting material. The solvent was removed in vacuo at RT. To the residue was added dry Et$_2$O, followed by removal of the solvent in vacuo. This step was performed three times in total, in order to remove any traces of TFA. Purification by preparative HPLC (acetate system; gradient: 0.5% per min, starting from 100% buffer a) yielded 11 mg of the title compound.

MS (MeOH; ESI-pos.): m/z=1565.2 [M+H]$^+$, 1587.2 [M+Na]$^+$, 783.4 [M+2H]$^{2+}$, 794.1 [M+Na+H]$^{2+}$.

Example 21

Cyanocobalamin-b-propyl-His-Re(CO)$_3$

Cyanocobalamin-b-acid (20.0 mg, 14.8 μmol) was dissolved in DMSO (0.8 ml). Subsequently were added DMF (2 ml) and NEt$_3$ (0.1 ml). In a different flask ca. 5 equivalents of [Re(methyl 3-aminopropyl-N-Teoc-histidinate)(CO)$_3$].CF3COOH (prepared via Boc-cleavage of the protected complex in CH$_2$Cl$_2$ and TFA (2/1 v/v) for 1 h at 0° C., followed by removal of the volatiles at RT in vacuo) were dissolved in a DMF/NEt$_3$ mixture (4.5 ml; 8/1 v/v). The two solutions were mixed, followed by addition of TBTU (32.1 mg, 0.1 mmol). After stirring at RT for 45 min, the solvent was removed in vacuo. The residue was purified by preparative HPLC (acetate system, gradient: 2.0% min$^{-1}$ starting from 100% buffer a) to afford 7 mg (73%) of cyanocobalamin-b-propyl-His-Re(CO)$_3$ MS (MeOH; ESI-pos.): 911.6 [M+2H]$^{2+}$, 923.2 [M+H+Na]$^{2+}$, 933.9 [M+2Na]$^{2+}$, 1822.1 [M+H]$^+$, 1845.6 [M+Na]$^+$.

Example 22

Cyanocobalamin-b-ethyl-Triamine

Triethylenetetramine (55.4 μl, 369 μmol) was dissolved in a mixture of DMF (2.5 ml) and water (2.5 ml). KCN (9.6 mg, 147 μmol) was added, and the pH was adjusted to 6 by addition of aqueous HCl. Cyanocobalamin-b-acid (10.0 mg, 7.4 μmol), EDC (5.7 mg, 29 μmol) and HOSu (3.4 mg, 29 μmol) were added. The same amounts of EDC and HOSu were added after 6 h, 24 h, 48 h and 120 h. HPLC analysis (acetate buffer) exhibited slow product formation, reaching a 75% conversion after 48 h which was not exceeded with prolonged stirring. After stirring for 144 h, the solvent was removed in vacuo and the product was purified by preparative HPLC using aqueous TFA 0.1% as buffer a and methanol as solvent b, with a gradient of 1% min$^{-1}$ starting from 80% buffer a. The product was isolated as cyanocobalamin-b-ethyl-Triamine×3TFA in a yield of 7.5 mg (55%).

ESI-MS: m/z=743.1 [M+2]$^{2+}$. UV/Vis: λ/nm (ε/mol l$^{-1}$cm$^{-1}$)=278.0 (13000), 316.0 (23100), 519.0 (6500), 549.0 (7200).

Example 23

Cyanocobalamin-b-ethyl-Triamine-Re(CO)$_3$

Cyanocobalamin-b-ethyl-Triamine (5 mg, 2.7 μmol) and (Et$_4$N)$_2$[ReBr$_3$(CO)$_3$] (2.2 mg, 2.9 μmol) were stirred in phosphate buffer, pH 7.4 (0.1 M, 0.33 ml) at 50° C. After 1 h, HPLC analysis showed full conversion of the starting materials into one product. After 4 h, the reaction mixture was desalted to give a product which is, according to HPLC analysis, a mixture of two stereoisomers in an approximate ratio of 2/1. The same pattern of two stereoisomers was found on labeling of cyanocobalamin-b-ethyl-Triamine with $^{99m}$Tc.

ESI-MS: m/z=1755.9 [M+1]$^+$, 878.5 [M+2]$^{2+}$.

Example 24

Cyanocobalamin-5'-phosphocolamin

A solution of cyanocobalamin (30 mg, 22.14 μmol), DCC (457 mg, 2.214 mmol) and M Fmoc-phosphocolamin (78.9 mg, 217.2 μmol) in dry DMF (2 ml) and dry pyridine (1 ml) was stirred under N$_2$ atmosphere at room temperature for 24 h. After addition of 2 ml of water the precipitated dicyclohexylurea was filtered off, and water and pyridine were evaporated at 60° C. under reduced pressure. The residual solution was diluted to a volume of 8 ml with a solution of 5% piperidine in DMF and stirred at room temperature for 2.5 h. The product was precipitated with diethyl ether, centrifuged and washed several times. The crude product was purified by prep. HPLC (gradient: 100%→20% a, 0%→80% MeOH in 30 min; a=0.1% AcOH, 10% acetonitrile in water; flow 10 ml/min.; column: M&N VP 250/21 Nucleosil 100-7 C18). Yield: 82% as a red solid.

$^{31}$P-NMR (5OO, CD$_3$OD) δ0.00 (s, 1P), 0.53 (s, 1P) MS (ESI+, MeOH): m/z=1478 [M+1]$^+$, 762 [M+2+2Na]$^{2+}$

Example 25

Cyanocobalamin-5'-phosphocolamin-His-OMe

Cyanocobalamin-5'-phosphocolamin (50 mg, 33.8 μmol) and methyl 1-(carboxymethyl)-N-Fmoc-histidinate hydrochloride (25 mg, 50.7 μmol) were dissolved in dry DMSO (4 ml) and the pH adjusted to 6-7 with 24 μl of DIPEA. BOP (45 mg, 101.5 μmol) was added to the solution as a solid and stirred at RT. After 1 h the pH of the reaction mixture got acidic and was adjusted to neutral again. After 5 h there was no starting material detectable by analytical HPLC. After precipitation with diethyl ether, the crude product was subjected to deprotection in a 1:1 mixture of DMF and piperidine (10 ml) for 1.5 h. After reprecipitation and purification with prep. HPLC as described for cyanocobalamin-5'-phosphocolamin (Example 24), the product was obtained in 46% yield.

$^{31}$P-NMR (500, D$_2$O) δ−2.16, −0.37; MS (ESI+, MeOH): m/z=1690 (M+1)$^+$, 845.6 (M+2)$^+$

Example 26

Cyanocobalamin-5'-phosphocolamin-His-Re(CO)$_3$

The same procedure was used as described for cyanocobalamin-5'-phosphocolamin-His-OMe (Example 25), using the Re(CO)$_3$ complex of 1-(carboxymethyl) histidinate instead of methyl 1-(carboxymethyl)-N-Fmoc-histidinate hydrochloride. The yield of the pure product was 37%.

$^{31}$P-NMR (500, D$_2$O, 333K) δ0.97, 2.23 MS (ESI+, MeOH): m/z=[M+1]$^+$ 1945, 929 (fragment) IR (KBr, cm$^{-1}$): 3400, 2128, 2020, 1901, 1902, 1664, 1499, 1399, 1219, 1073.

TABLE 2

Structure of cobalamin derivatives of formula (I), X = CN, of the Examples

| Example | R = H | R ≠ H | Spacer | Chelator | Spacer-chelator |
|---|---|---|---|---|---|
| 4 | $R^c$ = H, $R^d$ = H, $R^R$ = H | $R^b$: | ethyl-NHCOCH$_2$CH$_2$ (n = 2) | PAPAcet | (structure) |
| 5 | $R^c$ = H, $R^d$ = H, $R^R$ = H | $R^b$: | butyl-NHCOCH$_2$CH$_2$ (n = 4) | PAPAcet | |
| 6 | $R^c$ = H, $R^d$ = H, $R^R$ = H | $R^b$: | butyl-NHCOCH$_2$ (n = 4) | His-OMe | (structure) |
| 8 | $R^c$ = H, $R^d$ = H, $R^R$ = H | $R^c$: | butyl-NHCOCH$_2$CH$_2$ (n = 4) | PAPAcet | (structure) |
| 10 | $R^c$ = H, $R^d$ = H, $R^R$ = H | $R^b$: | ethyl- (n = 2) | PAMA-OEt | (structure) |
| 11 | $R^c$ = H, $R^d$ = H, $R^R$ = H | $R^b$: | propyl- (n = 3) | PAMA-OEt | |
| 12 | $R^c$ = H, $R^d$ = H, $R^R$ = H | $R^b$: | butyl (n = 4) | PAMA-OEt | |
| 13 | $R^c$ = H, $R^d$ = H, $R^R$ = H | $R^b$: | butyl (n = 4) | PAMA-OH | |
| 14 | $R^c$ = H, $R^d$ = H, $R^R$ = H | $R^b$: | hexyl- (n = 6) | PAMA-OEt | |
| 18 | $R^c$ = H, $R^d$ = H, $R^R$ = H | $R^d$: | propyl- (n = 3) | PAMA-Oet | |
| 20 | $R^c$ = H, $R^d$ = H, $R^R$ = H | $R^b$: | propyl- (n = 3) | His-OMe | (structure) |

TABLE 2-continued

Structure of cobalamin derivatives of formula (I), X = CN, of the Examples

| Example | R = H | R ≠ H | Spacer | Chelator | Spacer-chelator |
|---|---|---|---|---|---|
| 22 | $R^c$ = H<br>$R^d$ = H<br>$R^R$ = H | $R^b$: | ethyl-<br>(n = 2) | Triamine | 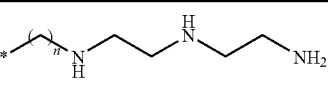 |
| 25 | $R^c$ = H<br>$R^d$ = H<br>$R^R$ = H | $R^R$: | phosphate-ethyl-<br>NHCOCH$_2$ | His-OMe | 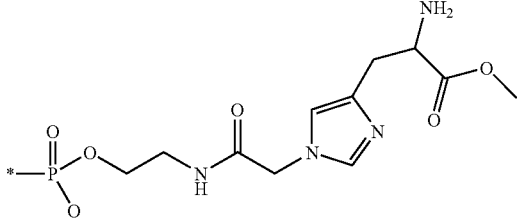 |

Example 27

General Labeling Procedure

Solutions of the precursor $[^{99m}Tc(OH_2)_3(CO)_3]^+$ were prepared out of $[^{99m}TcO_4]^-$ using a boranocarbonate kit as described by Alberto et al. (J. Am. Chem. Soc. 123, 3135-3136). A 10 ml glass vial with rubber stopper was flashed with N$_2$. 20 μl of a solution of cyano-cobalamin derivative (0.01 M in water), 20 μl of MES buffer (1.0 M) and 200 μl of a $[^{99m}Tc(OH_2)_3(CO)_3]^+$ solution were added and the reaction mixture was kept at 75° C. for 1 to 2 hours. HPLC analyses with γ-detection was performed to verify full conversion of the $^{99m}Tc$ species. Under these conditions, ester protecting groups in the chelators were cleaved to give the carboxylato complexes.

For in vivo studies and for binding studies to the transport vectors, very high specific activity was demanded. Therefore, 100 μl of the labeled solution were injected to an analytical HPLC system to separate the hot from the cold vitamin derivative. The eluate fraction with the highest gamma activity (ca. 300 μl) was diluted with normal saline to a concentration of 10 μCi per animal before i.v. injection. Separation condition were: acetate buffer, XTerra RP8 column, gradient: 0% methanol (0 min), 30% methanol (15 min), 100% methanol (25 min) for the b and d-derivatives, and the TEAP system as described by Schibli et al. (Bioconjugate Chem. 2000, 343-351) for the other compounds.

Example 28

Preparation of Transcobalamin II (TC II) from Rabbit Whole Blood

TC II is purified by affinity chromatography on a cyano-cobalamin-agarose matrix (Sigma), The gel (5 ml) is first washed with 200 ml 50 mM Tris/1 M NaCl, pH 8.0, afterwards with 200 ml 0.1 M glycine/0.1 M glucose/1 M NaCl pH 10, and again with 200 ml 50 mM Tris/1 M NaCl. 200 ml of twice centrifuged whole blood (first time 5000 rpm 15 min, second time 20'000 rpm 20 min at 4° C.) is applied to the affinity column, and the column washed sequentially as before. Bound TC II is eluted with 20 ml 4.0 Mguanidine HCl/50 mM Tris pH 8.0, and in a second step with 7.5 M guanidine HCl/50 mM Tris pH 8.0. Most of the bound TC II elutes already with 4 M guanidine HCl. Probes are dialyzed extensively against H$_2$O for 2 days at 4° C. Typical yields are 5-30 nmol/l which translates into 7.5-10 μg of TC II (MW: 50 kDa) per rabbit.

Example 29

Preparation of Transcobalamin II from Bacteria (Recombinant TCII)

Transcobalamin II cDNA is expressed in *E. coli* strain FA113, a K12 derivative with double knock-out in trxB and gor genes, where the cytoplasm forms an oxidizing environment and allows disulfide formation. The transcobalamin II protein contains a PreScission protease site followed by an N-terminal histidine tag. The protein is isolated from soluble fractions of *E. coli* extracts using nickel chelating sepharose. Cyanocobalamin is removed from the transcobalamin II bound to the chelating column with 8 M urea, and the transcobalamin II is afterwards released by imidazole. In some of the preparations, the His-tag is removed by a specific protease.

Example 30

Preparation of Transcobalamin I (TC I; Haptocorrin)

As a source of transcobalamin I, saliva of vegetarian human subjects is used. Saliva is centrifuged at 20'000 rpm 20 min at 4° C., mixed 1:1 with PBS and sterile filtered. The binding capacity of transcobalamin I is usually 10 ng/ml.

Example 31

Figure 1:
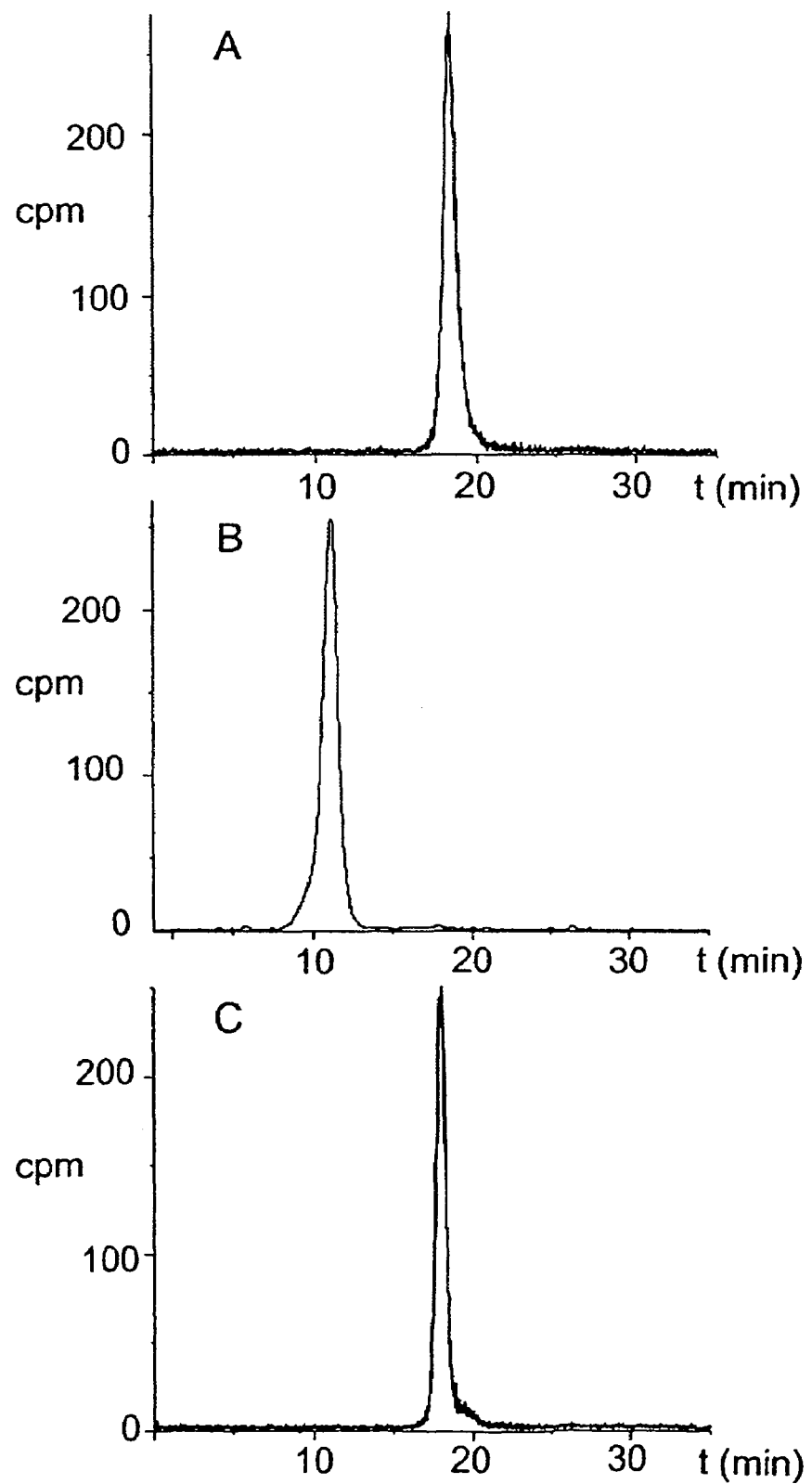
FIG. 1 is a graph illustrating the interaction of radioactive labelled cyanocobalamin-b- propyl-PAMA-OEt of Example 11, a TCII-non binder, with transport proteins in a gel shift assay. t=time, cpm=counts per minute.

Interaction of Cyanocobalamin Derivatives with Transport Proteins TC I and TC II) (FIG. 1 and FIG. 2)

The interaction of radiolabeled ($^{57}$Co, $^{99m}$Tc, $^{188}$Re, $^{111}$In) cyanocobalamin derivatives is measured by gel-shift assay. Radiolabeled cyanocobalamin (0.05 ng to 1 ng) is allowed to react with an excess of transport proteins for 15 min at room temperature. This mixture is applied to a gel-filtration column (Superdex75, Amersham Biosciencies) in the running buffer PBS and 0.1% Tween 20. Biologically active cyanocobalamin, which binds to transport proteins, shifts from a molecular weight of about 1.4 kDa to 40-70 kDa, depending on the transport protein. Titration of the binding capacity of the transport proteins is done with $^{57}$Co-cyanocobalamin (ICN Biomedicals GmbH, Germany; 10 µCi/50 ng).

Example 32

Labeling of Cyanocobalamin Derivatives with $^{188}$Re-Tricarbonyl

Preparation of $^{188}$Re-tricarbonyl and labeling of cyanocobalamin derivatives is done in a one pot reaction. 7.5 mg $BH_3NH_3$ is mixed with 20 mg sodium ascorbate, 100 µl cyanocobalamin derivatives ($10^{-3}$ M), 900 µl of a $[^{188}ReO_4]^-$ generator eluate (0.9% saline; 40 mCi to 270 mCi), 20 mg of $H_3PO_4$ (85%) and gassed with carbon monoxide (CO) for 20 min. The mixture is heated for ½ to 2 h at 60° C. and for ½ to 2 h at 90° C. The labeled cyanocobalamin is separated from the non-labeled on a reversed phase HPLC column (Waters Xterra RP8) in phosphate buffer with a linear methanol gradient. The active fraction is diluted with normal saline before i.v. injection to a concentration of 10 µCi per animal for imaging purposes and up to 2 mCi for therapeutic treatments.

Example 33

Sensitivity of Tumor Cell Spheroids to Ionizing Radiation

In radiobiology, the similarity of radiation response between spheroids and tumor xenograft bearing mice makes the spheroids to be a good alternative model to in vivo irradiation studies. Multicellular tumor spheroids are grown in spinner flasks with continuous stirring at 37° C. to an average diameter of 400 µm. Spheroids are harvested, washed in fresh medium and then incubated for 1 h with cold or $^{188}$Re-labeled cyano-cobalamin derivatives in 24 well flat bottom tissue culture plates. The dose range is 1 µCi to 20 µCi per well. Cytotoxicity is assessed by fluorescence viability markers, by measurements of the diameter of the whole spheroids and by a clonogenic assay of dispersed speroids in semi-solid agar.

Example 34

Figure 3:
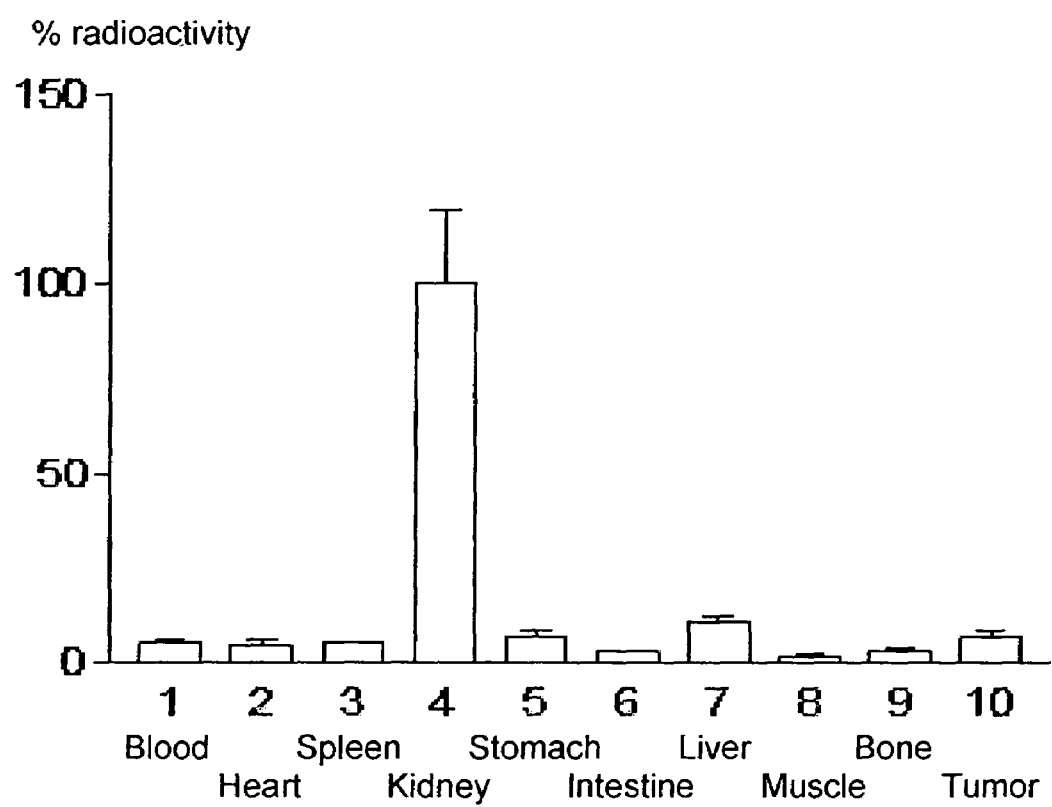

Biodistribution of Radiolabeled Cyanocobalamin Derivatives in Mice (FIG. 3, 4, 5, 6)

For biodistribution studies with $^{57}$Co-cyanocobalamin, 0.2 µCi/1 ng of the radiolabeled cyanocobalamin is mixed with 180 µl normal saline and injected i.v. in tumor bearing balb/c mice (syngeneic mouse melanoma B16-F10). After a specified time (5 min to 24 h), animals are sacrificed, the organs weighted and counted on a gamma counter. For biodistribution studies with $^{99m}$Tc-labeled cyanocobalamin, 10 µCi/0.5 ng of the radiolabelled cyanocobalamin is mixed with normal saline and used as before. For biodistribution with $^{111}$In-labeled cyanocobalamin, 2 µCi/5 ng of the radiolabeled cyanocobalamin is mixed with normal saline and used as before. To study the effect of Vitamin B12 deficient food, the biodistribution of labeled cyanocobalamin is compared in mice fed with normal food with the biodistribution in mice fed with vitamin B12 deficient food for a period of 2 weeks.

Example 35

Therapy Studies with $^{188}$Re-Labeled Cyanocobalamin Derivatives in Tumor Bearing Mice For therapy studies, syngeneic melanoma tumor is grown in balb/c mice to a size of about 200 mg (measured by caliber). Increasing doses (0.1 to 2 mCi) of radiolabeled cyanocobalamin constructs and of cold constructs are injected i.v. Tumor volume is assessed by measurement with a caliber. When the tumor reaches a size of 800 mg, animals are sacrificed. In a series of experiments animals are treated with a fractionated regiment: radiolabeled cyanocobalamin is given 3 times a week apart. Animals are observed for 60 days for re-growth of tumors.

The invention claimed is:

1. A cobalamin derivative of formula (1):

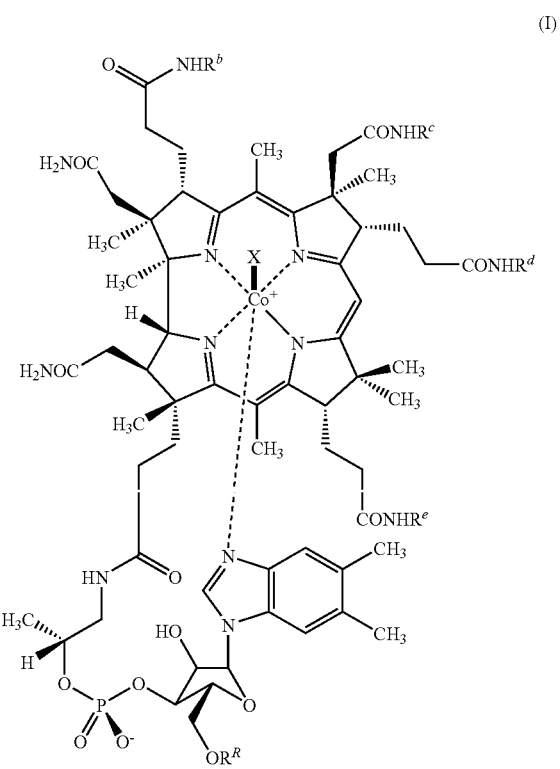

(I)

wherein:
(i) $R^b$ is a spacer-chelator group optionally carrying a metal atom;
(ii) $R^c$, $R^d$, and $R^e$ are an antibiotic or antiproliferative therapeutic agent, or hydrogen; and $R^R$ is an antibiotic or antiproliferative therapeutic agent connected through a linker Z, or hydrogen, wherein the linker Z is selected from the group consisting of phosphates, phosphonates, carboxylic esters, alkylenes of 1 to 10 carbon atoms, and combinations thereof;
(iii) with the proviso that at least one of the residues $R^c$, $R^d$, $R^e$ and $R^R$ are hydrogen;
(iv) X is cyano, methyl, hydroxy, aquo or a 5'-deoxyadenosyl group; and
(v) the central cobalt (Co) atom is optionally in the form of a radioactive isotope; and wherein the spacer-chelator group consists of an aliphatic chain of 2 to 4 carbon atoms carrying a chelator selected from the chelators of formulae (II) to (IX):

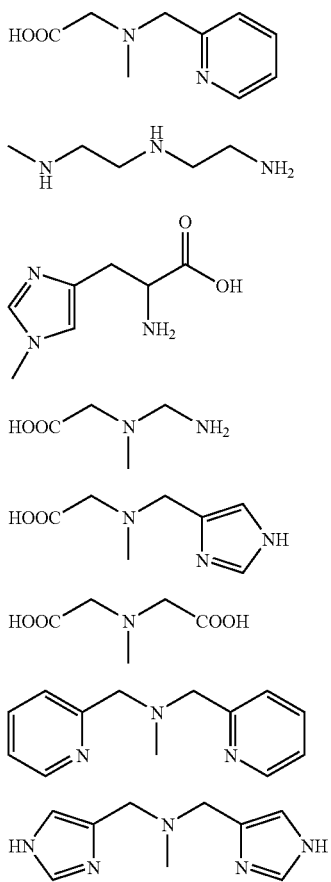

wherein carboxyl groups in formulae (II) to (IX) may be present as esters; and
said cobalamin derivative:
(a) has no binding affinity or less than 20% binding affinity to transcobalamin II when compared to the binding affinity of non-modified cobalamin in a binding test, and
(b) retains activity as a vitamin B12 substitute.

2. The cobalamin derivative according to claim 1 retaining more than 2% of the activity as a vitamin B12 substitute in a growth assay.

3. The cobalamin derivative according to claim 1
(a) having less than 10% of binding affinity to transcobalamin II when compared to the binding affinity of non-modified cobalamin in a binding test, and
(b) retaining more than 10% of the activity as a vitamin B12 substitute in a growth assay.

4. The cobalamin derivative according to claim 1
(a) having less than 5% of binding affinity to transcobalamin II when compared to the binding affinity of non-modified cobalamin in a binding test, and
(b) retaining more than 10% of the activity as a vitamin B12 substitute in a growth assay.

5. The cobalamin derivative according to claim 1 carrying a therapeutic and/or diagnostic agent.

6. The cobalamin derivative according to claim 1 carrying a radioactive metal.

7. The cobalamin derivative according to claim 6 wherein the radioactive metal is $^{94m}$Tc, $^{99m}$Tc, $^{188}$Re, $^{186}$Re, $^{111}$In, $^{90}$Y, $^{64}$Cu, $^{67}$Cu or $^{177}$Lu.

8. The cobalamin derivative according to claim 1 wherein X is cyano.

9. The cobalamin derivative according to claim 1, wherein the central cobalt atom is the radioisotope $^{57}$Co or $^{60}$Co.

10. The cobalamin derivative according to claim 1, wherein
$R^b$ is a spacer-chelator group optionally carrying a metal atom, the spacer is an aliphatic chain of 2 to 4 carbon atoms, and the chelator is of formula (II), wherein the group COOH is optionally in the form of an ester;
$R^c$, $R^d$, $R^e$ and $R^R$ are hydrogen; and
X is cyano.

11. The cobalamin derivative according to claim 10, wherein
$R^b$ is a spacer-chelator group optionally carrying a metal atom, the spacer is an aliphatic chain of 4 carbon atoms, and the chelator is of formula (II), wherein the group COOH is in the form of the ethyl ester;
$R^c$, $R^d$, $R^e$ and $R^R$ are hydrogen; and
X is cyano.

12. The cobalamin derivative according to claim 1, wherein
$R^d$ is a spacer-chelator group optionally carrying a metal atom, the spacer is an aliphatic chain of 3 carbon atoms, and the chelator is of formula (II), wherein the group COOH is optionally in the form of an ester;
$R^b$, $R^c$, $R^e$ and $R^R$ are hydrogen; and
X is cyano.

13. The cobalamin derivative according to claim 1, wherein
$R^b$ is a spacer-chelator group optionally carrying a metal atom, the spacer is an aliphatic chain of 2 carbon atoms, and the chelator is of formula (III);
$R^c$, $R^d$, $R^e$ and $R^R$ are hydrogen; and
X is cyano.

14. A pharmaceutical composition comprising a cobalamin derivative according to claim 1.

15. A method of diagnosis of a neoplastic disease in a mammal comprising
(a) exposing the mammal suspected of being inflicted by a neoplastic disease to a period of a vitamin B12-free diet, and
(b) subsequently applying a cobalamin derivative according to claim 1 carrying a diagnostic agent.

16. A method of treatment of a mammal suffering from melanoma comprising
(a) exposing the mammal in need of treatment to a period of a vitamin B12-free diet, and
(b) subsequently applying a cobalamin derivative according to claim 1 carrying a therapeutic agent.

17. The method of claim 15, wherein the cobalamin is effective in cancer imaging.

* * * * *